United States Patent [19]

Kodaka et al.

[11] Patent Number: 5,532,365
[45] Date of Patent: Jul. 2, 1996

[54] INTERMEDIATE FOR FURANYL INSECTICIDE

[75] Inventors: Kenji Kodaka; Katsutoshi Kinoshita; Takeo Wakita; Shirou Shiraishi; Kazutomi Ohnuma; Eiichi Yamada; Naoko Yasui; Michihiko Nakaya; Hirozumi Matsuno; Nobuyuki Kawahara, all of Chiba-ken; Koichi Ebihara, Fukuoka-ken, all of Japan

[73] Assignee: Mitsui Toatsu Chemicals, Inc., Tokyo, Japan

[21] Appl. No.: 417,111

[22] Filed: Apr. 5, 1995

Related U.S. Application Data

[62] Division of Ser. No. 326,260, Oct. 20, 1994, Pat. No. 5,434,181.

[30] Foreign Application Priority Data

Oct. 26, 1993 [JP] Japan ..................... 5-266799

[51] Int. Cl.⁶ .......................................... C07D 251/08
[52] U.S. Cl. .......................................... 544/212
[58] Field of Search ............................... 544/212

[56] References Cited

FOREIGN PATENT DOCUMENTS

| | | |
|---|---|---|
| 192060 | 8/1986 | European Pat. Off. . |
| 493369 | 7/1992 | European Pat. Off. . |
| 595125 | 5/1994 | European Pat. Off. . |
| 64-70468 | 3/1989 | Japan . |
| 2-171 | 1/1990 | Japan . |
| 3-157308 | 7/1991 | Japan . |
| 4-154741 | 5/1992 | Japan . |
| 5-9173 | 1/1993 | Japan . |
| WO91/04965 | 4/1991 | WIPO . |

OTHER PUBLICATIONS

Minamida et al, J. Pesticide Sci., vol. 18, pp. 41–48 (1993).
Gompper et al, Chem. Ber., vol. 100, pp. 591–604 (1967).

*Primary Examiner*—Bernard Dentz
*Attorney, Agent, or Firm*—Burns, Doane, Swecker & Mathis

[57] ABSTRACT

The present invention relates to novel (tetrahydro-3-furanyl)methylamino derivatives of the following formula (1):

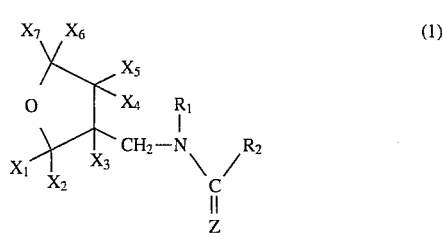

wherein the variables are defined in the specification, which are useful as insecticides.

3 Claims, No Drawings

INTERMEDIATE FOR FURANYL INSECTICIDE

This application is a divisional of application Ser. No. 08/326,260, filed Oct. 20, 1992, now U.S. Pat. No. 5,434,181.

BACKGROUND OF THE INVENTION

1. Field of the Invention

The present invention relates to novel (tetrahydro-3-furanyl)methylamine derivatives, insecticides containing the derivatives as an effective ingredient and intermediates thereof.

2. Description of the Prior Art

Heretofore, a lot of amine compounds having a nitromethylene group, a nitroimino group or a cyanoimino group have been known (Japanese Patent Laid-Open Nos. 070468/1989, 171/1990, 157308/1991 and 154741/1992, and others). In these publications, there is a description that the amine compounds which contain a heterocyclic group in their molecule show an insecticidal activity. However, when the present inventors synthesized these compounds and examined their insecticidal activity, it was found that not all of the amine derivatives having a heterocyclic group showed insecticidal activity. In other words, compounds showing a noticeable activity among the compounds described in these publications are limited to the amine derivatives having a thiazolylmethyl or pyridylmethyl group as the heterocyclic group, and this fact is described in J. Pesticide Sci. 18 41 (1993) and others. Further, the compounds which are planned to commercialize at present are only the derivatives having a pyridylmethyl group as the heterocyclic group.

SUMMARY OF THE INVENTION

Accordingly, it is an object of the present invention to provide amine derivatives having a nitro-methylene group, a nitroimino group or a cyanoimino group, which are low-toxic and show excellent insecticidal activity without having the above-mentioned pyridylmethyl group or thiazolylmethyl group as the heterocyclic group.

The present inventors earnestly investigated so as to solve the above-mentioned problems and, as a result, have found that novel (tetrahydro-3-furanyl)methylamine derivatives of the formula (1) have an excellent insecticidal activity even in the absence of a pyridylmethyl group or a thiazolylmethyl group in their molecular structure. On the basis of the finding, they have completed the present invention.

According to the present invention, there are provided (tetrahydro-3-furanyl)methylamine derivatives represented by a formula (1):

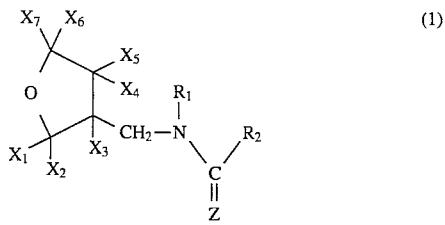
(1)

where $X_1$, $X_2$, $X_3$, $X_4$, $X_5$, $X_6$ and $X_7$ represent each a hydrogen atom or an alkyl group having from 1 to 4 carbon atoms; $R_1$ represents a hydrogen atom, an alkyl group having from 1 to 5 carbon atoms, an alkenyl group having 3 carbon atoms, a benzyl group, an alkoxyalkyl group having from 2 to 4 carbon atoms (in its whole group), an alkyloxycarbonyl group having from 1 to 3 carbon atoms, a phenoxy carbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group or an N,N-dimethylcarbamoyl group; $R_2$ represents a hydrogen atom, an amino group, a methyl group, an alkylamino group having from 1 to 5 carbon atoms, a di-substituted alkylamino group having from 2 to 5 carbon atoms (in its whole group), a 1-pyrrolidinyl group, an alkenylamino group having 3 carbon atoms, an alkynylamino group having 3 carbon atoms, a methoxyamino group, an alkoxyalkylamino group having from 2 to 4 carbon atoms (in its whole group), a methylthio group or $-N(Y_1)Y_2$ (where $Y_1$ represents an alkyloxycarbonyl group having from 1 to 3 carbon atoms, a phenoxycarbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group, an N,N-dimethylcarbamoyl group, a (tetrahydro-3-furanyl)methYl group or a benzyl group, and $Y_2$ represents a hydrogen atom or an alkyl group having from 1 to 5 carbon atoms); and Z represents $=N-NO_2$, $=CH-NO_2$ or $=N-CN$; insecticides containing the derivatives as an effective ingredient; and intermediates for producing the compounds of the formula (1) represented by a formula (2):

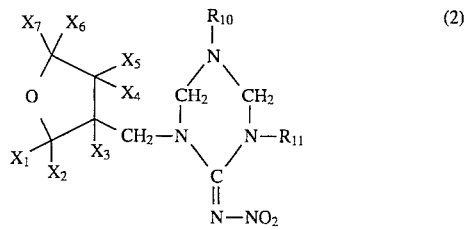
(2)

where $X_1$, $X_2$, $X_3$, $X_4$, $X_5$, $X_6$ and $X_7$ represent each a hydrogen atom or an alkyl group having from 1 to 4 carbon atoms; $R_{10}$ represents an alkyl group having from 1 to 5 carbon atoms or a benzyl group; and Rll represents an alkyl group having from 1 to 5 carbon atoms or a benzyl group.

The novel (tetrahydro-3-furanyl)methylamine derivatives of the formula (1) according to the invention are excellent compounds having a high insecticidal power and broad insecticidal spectrum. Further, agricultural chemicals containing the novel (tetrahydro-3-furanyl)methylamine derivatives of the formula (1) according to the invention have outstanding characteristics as insecticides and hence are useful.

DETAILED DESCRIPTION OF THE INVENTION

Specific examples of the alkyl group for $X_1$, $X_2$, $X_3$, $X_4$, $X_5$, $X_6$, and $X_7$ in the above formulae (1) and (2) include a methyl group, an ethyl group, an n-propyl group, an iso-propyl group, a tert-butyl group, and the like, preferably a methyl group.

Specific examples of the alkyl group for $R_1$ include a methyl group, an ethyl group, an n-propyl group, an iso-propyl group, an n-butyl group, an iso-butyl group, a sec-butyl group, a tert-butyl group, an n-pentyl group, and the like.

Specific examples of the alkenyl group for $R_1$ include a 1-propenyl group, a 2-propenyl group, and the like.

Specific examples of the alkoxyalkyl group for $R_1$ include a methoxymethyl group, an ethoxymethyl group, an n-propoxymethyl group, an iso-propoxymethyl group, a methoxyethyl group, an ethoxyethyl group, and the like.

Specific examples of the alkyloxycarbonyl group for $R_1$ include a methyloxycarbonyl group, an ethyloxycarbonyl group, an n-propyloxycarbonyl group, an iso-propyloxycarbonyl group, and the like.

Specific examples of the alkylcarbonyl group for $R_1$ include a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group, a tert-butylcarbonyl group, an n-pentylcarbonyl group, an n-hexylcarbonyl group, and the like.

Specific examples of the alkenylcarbonyl group for $R_1$ include a vinylcarbonyl group, a 1-methylvinylcarbonyl group, and the like.

Specific examples of the cycloalkylcarbonyl group for $R_1$ include a cyclopropylcarbonyl group, a cyclobutylcarbonyl group, a cyclopentylcarbonyl group, a cyclohexylcarbonyl group, and the like.

Specific examples of the benzoyl group substituted by alkyl group(s) for $R_1$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) for $R_1$ include a 2-chlorobenzoyl group, a 3-chlorobenzoyl group, a 4-chlorobenzoyl group, a 3,4-dichloro-benzoyl group, a 4-fluorobenzoyl group, and the like.

Although $R_1$ can take various substituents as described above, it is preferably a hydrogen atom, an alkylcarbonyl group having from 1 to 4 carbon atoms or a cyclopropylcarbonyl group.

Specific examples of the alkylamino group for $R_2$ include a methylamino group, an ethylamino group, an n-propylamino group, an iso-propylamino group, an n-butylamino group, an iso-butylamino group, a sec-butylamino group, a tert-butylamino group, an n-pentylamino group, and the like, preferably a methylamino group.

Specific examples of the di-substituted alkylamino group for $R_2$ include a dimethylamino group, a diethylamino group, an N-methyl-N-ethylamino group, an N-methyl-N-n-propylamino group, an N-methyl-N-n-butylamino group, and the like, preferably a dimethylamino group.

Specific examples of the alkenylamino group for $R_2$ include a 1-propenylamino group, a 2-propenylamino group, and the like.

Specific examples of the alkynylamino group for $R_2$ include a propargylamino group, and the like.

Specific examples of the alkoxyalkylamino group for $R_2$ include a methoxymethylamino group, an ethoxymethylamino group, an n-propoxymethylamino group, an iso-propoxymethylamino group, a methoxyethylamino group, an ethoxyethylamino group, and the like.

Specific examples of the alkyloxycarbonyl group denoted by $Y_1$ for $R_2$ include a methyloxycarbonyl group, an ethyloxy-carbonyl group, an n-propyloxycarbonyl group, an iso-propyloxy-carbonyl group, and the like.

Specific examples of the alkylcarbonyl group denoted by $Y_1$ for $R_2$ include a methylcarbonyl group, an ethylcarbonyl group, an n-propylcarbonyl group, an iso-propylcarbonyl group, an n-butylcarbonyl group, an iso-butylcarbonyl group, a sec-butyl-carbonyl group, a tert-butylcarbonyl group, an n-pentylcarbonyl group, an n-hexylcarbonyl group, and the like, preferably a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group and a tert-butylcarbonyl group.

Specific examples of the alkenylcarbonyl group denoted by $Y_1$ for $R_2$ include a vinylcarbonyl group, a 1-methylvinylcarbonyl group, and the like.

Specific examples of the cycloalkylcarbonyl group denoted by $Y_1$ for $R_2$ include a cyclopropylcarbonyl group, a cyclobutylcarbonyl group, a cyclopentylcarbonyl group, a cyclo-hexylcarbonyl group, and the like, preperably a cyclopropyl-carbonyl group.

Specific examples of the benzoyl group substituted byalkyl group(s) denoted by $Y_1$ for $R_2$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) denoted by $Y_1$ for $R_2$ include a 2-chlorobenzoyl group, a 3-chlorobenzoyl group, a 4-chlorobenzoyl group, a 3,4-dichlorobenzoyl group, a 4-fluoro benzoyl group, and the like.

Specific examples of the alkyl group denoted by $Y_2$ for $R_2$ include a methyl group, an ethyl group, an n-propyl group, an iso-propyl group, an n-butyl group, an iso-butyl group, a sec-butyl group, a tert-butyl group, an n-pentyl group, and the like, preferably a methyl group.

In the formula (1), compounds in which $R_1$ and $Y_1$ are concurrently an alkylcarbonyl group having from 1 to 4 carbon atoms or a cyclopropylcarbonyl group are preferred from the viewpoint of both insecticidal activity and production method.

Compounds of the formula (1) may be produced in accordance with any of the following methods (A) through (F) depending of the substituents involved.

Method (A):

The production of compounds of an formula (1A) where $R_1$ stands for $R_3$ and $R_2$ for $NR_5R_6$ in the formula (1) is shown by a reaction scheme (I):

Reaction Scheme (I):

-continued
Reaction Scheme (I):

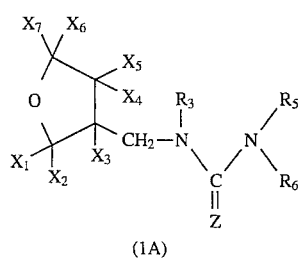

(1A)

where $X_1$, $X_2$, $X_3$, $X_4$, $X_5$, $X_6$ and $X_7$ have the same meanings as mentioned above; $R_3$ represents a hydrogen atom, an alkyl group having from 1 to 5 carbon atoms, an alkenyl group having 3 carbon atoms, a benzyl group or an alkoxyalkyl group having from 2 to 4 carbon atoms; $R_4$ represents an alkylthio group having from 1 to 5 carbon atoms or a benzylthio group; $R_5$ represents an alkyl group having from 1 to 5 carbon atoms, an alkenyl group having 3 carbon atoms, an alkynyl group having 3 carbon atoms, a methoxy group, an alkoxyalkyl group having from 2 to 4 carbon atoms, a (tetrahydro-3-furanyl)methyl group or a benzyl group; $R_6$ represents a hydrogen atom or an alkyl group having from 1 to 5 carbon atoms, or $R_5$ and $R_6$ are bonded together to form a 1-pyrrolidinyl group; and Z has the same meaning as mentioned above.

Namely, the compounds of the formula (1A) may be produced with ease by reacting a compound of the formula (3) and an amine of the formula (4) in various solvents in the presence of a base or a catalyst as occasion demands.

As the base, it is possible to use an excessive amount of the amine, or a carbonate such as potassium carbonate and sodium carbonate, a phosphate such as tripotassium phosphate, trisodium phosphate, dipotassium hydrogenphosphate and disodium hydrogenphosphate, an acetate such as sodium acetate and potassium acetate, or the like.

As the catalyst, it is possible to use an organic base such as 4-(dimethylamino)pyridine, DBU, triethylamine and diazabicycloundecene, ion exchange resin, silica gel, zeolite, or the like.

The solvent to be used may include not only water but also alcohols such as methanol, ethanol, propanol and butanol, aromatic hydrocarbons such as benzene, toluene and xylene, aliphatic hydrocarbons such as hexane, heptane and petroleum benzine, aprotic polar solvents such as dimethylformamide, dimethylacetamide, dimethylsulfoxide, 1,3-dimethyl-2-imidazolidinone and 1-methyl- 2-pyrrolidinone, ethers such as ethyl ether, diisopropyl ether, 1,2-dimethoxyethane, tetrahydrofuran and dioxane, nitriles such as acetonitrile and propionitrile, ketones such as acetone and diisopropyl ketone, and the like.

The reaction temperature and the reaction time can be varied over wide ranges. In general, the reaction temperature is in the range of from −20° to 200° C., preferably from 0° to 150° C.; and the reaction time is in the range of from 0.01 to 50 hours, preferably from 0.1 to 15 hours.

The compounds of the formula (3) in the reaction scheme (I) can be produced in accordance with, for example, a procedure described in Japanese Patent Laid-Open No. 70468/1989. The compounds of the formulae (4) in the reaction scheme (I) can be produced by methods known in the art.

Method B:

The production of compounds of an formula (1B) where $R_1$ stands for $R_7$ and $R_2$ for $R_8$ in the formula (1) is shown by a reaction scheme (II):

Reaction Scheme (II):

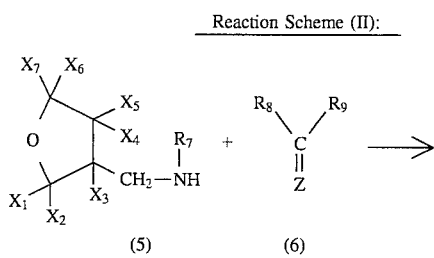

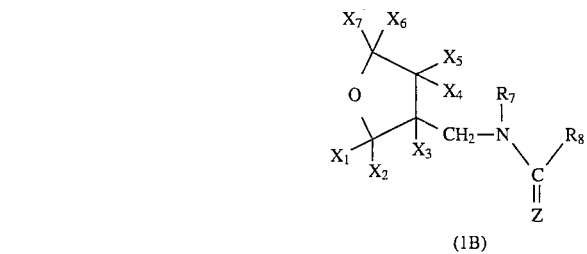

(1B)

where $X_1$, $X_2$, $X_3$, $X_4$, $X_5$, $X_6$ and $X_7$ have the same meanings as mentioned above; $R_7$ is a hydrogen atom, an alkyl group having from 1 to 5 carbon atoms, an alkenyl group having 3 arbon atoms, a benzyl group or an alkoxyalkyl group having from 2 to 4 carbon atoms; $R_8$ represents a hydrogen atom, an amino group, an alkyl group having from 1 to 3 carbon atoms, an alkylamino group having from 1 to 5 carbon atoms, a di-substituted alkylamino group having from 2 to 5 carbon atoms, a 1-pyrrolidinyl group, an alkenylamino group having 3 carbon atoms, an alkynylamino group having 3 carbon atoms, a methoxyamino group, an alkoxyalkylamino group having from 2 to 4 carbon atoms, an alkylthio group having from 1 to 5 carbon atoms or a benzylthio group; $R_9$ represents an amino group, an alkoxy group having from 1 to 5 carbon atoms, an alkylthio group having from 1 to 5 carbon atoms or an benzylthio group; and Z has the same meaning as described above.

Namely, the compounds of the formula (1B) may be produced with ease and in high yield by reacting a compound of the formula (5) and a compound of the formula (6).

The reaction is effected with ease in various solvents in the presence of a base or a catalyst as occasion demands.

As the base, it is possible to use a carbonate such as potassium carbonate and sodium carbonate, a phosphate such as tripotassium phosphate, trisodium phosphate, dipotassium hydrogenphosphate and disodium hydrogenphosphate, an acetate such as sodium acetate and potassium acetate, or the like.

As the catalyst, it is possible to use an organic base such as 4-(dimethylamino)pyridine, DBU, triethylamine and diazabicycloundecene, a sulfonic acid such as p-toluenesulfonic acid and methanesulfonic acid, a mineral acid such as sulfuric acid, hydrogen chloride and phosphoric acid, ion exchange resin, silica gel, zeolote, or the like.

The solvent to be used may include not only water but also alcohols such as methanol, ethanol, propanol and butanol, aromatic hydrocarbons such as benzene, toluene and xylene, aliphatic hydrocarbons such as hexane, heptane and petroleum benzine, aprotic polar solvents such as dimethylformamide, dimethylacetamide, dimethylsulfoxide, 1,3-dimethyl-2-imidazolidinone and 1-methyl- 2-pyrrolidinone, ethers such as ethyl ether, diisopropyl ether, 1,2- dimethoxyethane, tetrahydrofuran and dioxane, nitriles such as acetonitrile and propionitrile, ketones such as acetone and diisopropyl ketone, and the like.

The reaction temperature and the reaction time can be varied over wide ranges. In general, the reaction temperature is in the range of from −20° to 200° C., preferably from 0° to 150° C.; and the reaction time is in the range of from 0.01 to 50 hours, preferably from 0.1 to 15 hours.

The compounds of a formula (5) in the reaction scheme (II) may be produced in accordance with procedures of a reaction scheme (IIA):

Reaction Scheme (IIA):

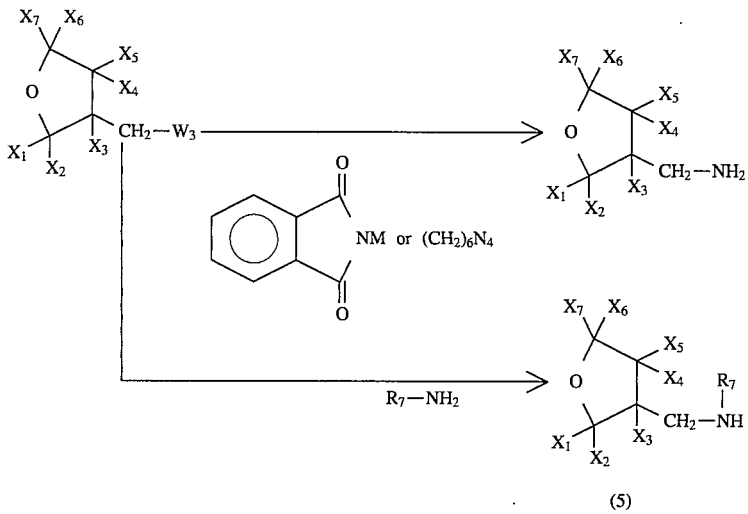

(5)

where $X_1$, $X_2$, $X_3$, $X_4$, $X_5$, $X_6$ and $X_7$ have the same meanings as described above; $W_3$ represents a halogen atom, a toluenesulfonyloxy group, a methanesulfonyloxy group or a trifluoromethanesulfonyloxy group; and M represents a sodium atom or a potassium atom; $R_7$ represents a hydrogen atom, an alkyl group having from 1 to 5 carbon atoms, an alkenyl group having 3 carbon atoms, a benzyl group or an alkoxyalkyl group having from 2 to 4 carbon atoms.

Namely, the compounds of the formula (5) can be produced by halogenating (tetrahydro-3-furanyl)methanol derivatives with a halogenating agent such as thionyl chloride, phosphorus oxychloride, phosphorus tribromide, triphenyl-phosphine/carbon tetrabromide and triphenylphosphine/carbon tetrachloride, or sulfonating the derivatives with a sulfonating agent such as tosyl chloride, methanesulfonyl chloride and trifluoromethane-sulfonic acid anhydride, followed by reaction according to known amine synthesis methods such as the Gabriel Synthesis using potassium phthalimide and the Delépine Reaction using hexamethylenetetramine or by reacting with an alkylamine.

The compounds of the formula (6) in the reaction scheme (II) can be produced by a procedure described in Chem. Ber., vol. 100, p591, and others.

Method (C):

The production of compounds of a formula (1C) where $R_1$ stands for $R_7$, $R_2$ for $SW_1$ and Z for $=N-NO_2$ in the formula (1) is shown by a reaction scheme (III).

Reaction Scheme (III):

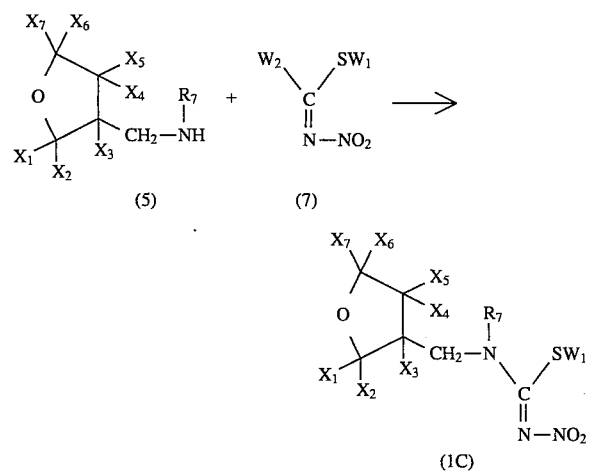

where $X_1$, $X_2$, $X_3$, $X_4$, $X_5$, $X_6$ and $X_7$ have the same meaning as described above; $R_7$ represents a hydrogen atom, an alkyl group having from 1 to 5 carbon atoms, a benzyl group or an alkoxyalkyl group having from 2 to 4 carbon atoms; $W_1$ represents an alkyl group having from 1 to 4 carbon atoms; and $W_2$ represents an imide group.

Namely, the compounds of the formula (1C) can be produced with ease and in high yield by reacting a compound of the formula (5) with a compound of the formula (7).

The reaction is effected with ease in various solvents in the presence of a base as occasion demands.

The base to be used includes alkali metal hydroxides such as sodium hydroxide and potassium hydroxide, alkaline earth metal hydroxide such as magnesium hydroxide and calcium hydroxide, alkali metal hydrides such as sodium hydride and potassium hydride, alkali metal alcoholares such as sodium methylate and sodium ethylate, alkali metal oxides such as sodium oxide, carbonates such as potassium carbonate and sodium carbonate, phosphates such as tripotassium phosphate, trisodium phosphate, dipotassium hydrogenphosphate and disodium hydrogenphosphate,. acetates such as sodium acetate and potassium acetate, organic bases such as pyridine, 4-(dimethylamino)pyridine, DBU, triethylamine and diazabicycloundecene, and the like.

The solvents to be used may include not only water but also alcohols such as methanol, ethanol, propanol and butanol, aromatic hydrocarbons such as benzene, toluene and xylene, aliphatic hydrocarbons such as hexane, heptane and petroleum benzine, aprotic polar solvents such as dimethylformamide, dimethylacetamide, dimethylsulfoxide, 1,3-dimethyl-2-imidazolidinone and 1-methyl- 2-pyrrolidinone, ethers such as ethyl ether, diisopropyl ether, 1,2-dimethoxyethane, tetrahydrofuran and dioxane, nitriles such as acetonitrile and propionitrile, ketones such as acetone and diisopropyl ketone, and the like.

The reaction temperature and the reaction time can be varied over wide ranges. In general, the reaction temperature is in the range from −30° to 200° C., preferably from −20° to 150° C.; and the reaction time is in the range of 0.01 to 50 hours, preferably from 0.1 to 15 hours.

The compound of the formula (5) in the reaction scheme (III) can be produced by the procedure of the above-described reaction scheme (IIA).

The compound of the formula (7) in the reaction scheme (III) can be produced in accordance with procedures of Japanese Patent Laid-Open No. 9173/1993 and others.

Method (D):

The production of compounds of a formula (1D) where $R_1$ stands for $Y_1$, $R_2$ for $NY_1Y_3$, and $Z$ for $Z_1$ in the formula (1) is shown by a reaction scheme (IV):

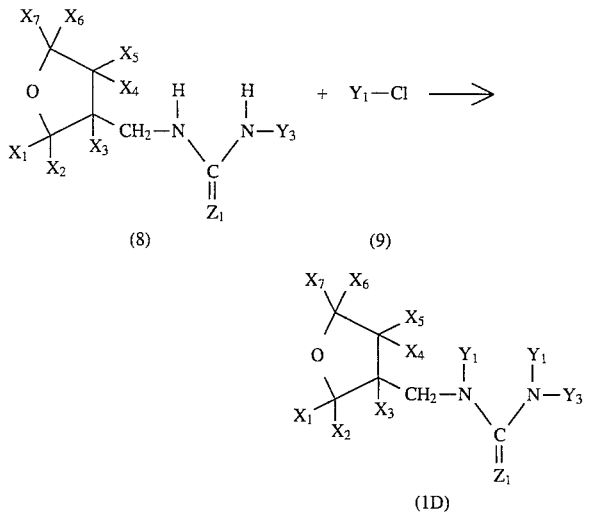

where $X_1$, $X_2$, $X_3$, $X_4$, $X_5$, $X_6$ and $X_7$ have the same meaning as described above; $Y_3$ represents a hydrogen atom or an alkyl group having from 1 to 5 carbon atoms; $Y_1$ represents an alkyloxycarbonyl group having from 1 to 3 carbon atoms, a phenoxycarbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 atoms, a benzoyl group substituted by halogen atom(s), a 2-furanyl-carbonyl group, or an N,N-dimethylcarbamoyl group; and $Z_1$ represents =N—NO$_2$ or =N—CN.

The compounds of the formula (1D) may be produced with ease and in high yield by reacting. a compound of the formula (8) with a compound of the formula (9).

The reaction is effected with ease in various solvents in the presence of a base.

The base to be used includes alkali metal hydroxides such as sodium hydroxide and potassium hydroxide, alkaline earth metal hydroxides such as magnesium hydroxide and calcium hydroxide, alkali metal hydrides such as sodium hydride and potassium hydride, alkali metal alcoholates such as sodium methylate and sodium ethylate, alkali metal oxides such as sodium oxide, carbonates such as potassium carbonate and sodium carbonate, phosphates such as tripotassium phosphate, trisodium phosphate, dipotassium hydrogenphosphate and disodium hydrogenphosphate, acetates such as sodium acetate and potassium actate, organic bases such as pyridine, 4-(dimethylamino)pyridine, DBU, triethylamine and diazabicycloundecene, and the like.

The solvents to be used may include not only water but also alcohols such as methanol, ethanol, propanol and butanol, aromatic hydrocarbons such as benzene, toluene and xylene, aliphatic hydrocarbons such as hexane, heptane and petroleum benzine, aprotic polar solvents such as dimethylformamide, dimethylacetamide, dimethylsulfoxide, 1,3-dimethyl-2-imidazolidinone and 1-methyl- 2-pyrrolidinone, ethers such as ethyl ether, diisopropyl ether, 1,2-dimethoxyethane, tetrahydrofuran and dioxane, nitriles such as acetonitrile and propionitrile, ketones such as acetone and diisopropyl ketone, chlorinated solvents such as methylene chloride and chloroform, and the like.

The reaction temperature and the reaction time can be varied over wide ranges. In general, the reaction temperature is in the range of from −20° to 200° C., preferably from 0°–150° C.; and the reaction time is in the range of from 0.01 to 50 hours, preferably from 0.1 to 15 hours.

The compound of the formula (8) in the reaction scheme (IV) can be produced in accordance with the procedure of the reaction scheme (I) or (II).

The compound of the formula (9) in the reaction scheme (IV) can be produced from known carboxylic acids in accordance with known methods for the synthesis of acid chlorides.

Method (E):

The production of compounds of a formula (1E) where $R_1$ stands for $Y_1$, $R_2$ for $NY_4Y_5$, and Z for $Z_1$ is shown by a reaction scheme (V):

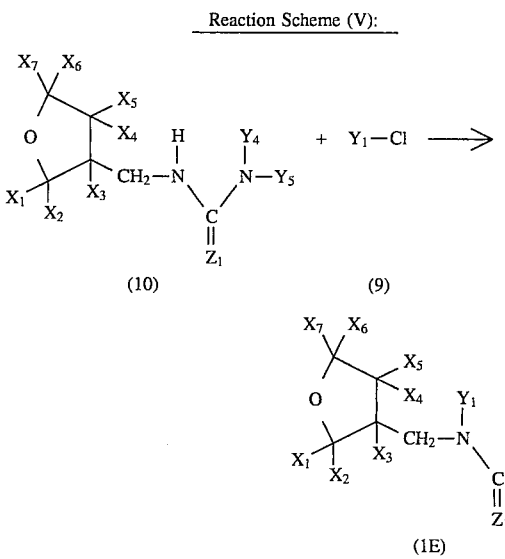

where $X_1$, $X_2$, $X_3$, $X_4$, $X_5$, $X_6$ and $X_7$ have the same meanings as described above; $Y_4$ represents an alkyl group having from 1 to 5 carbon atoms; $Y_5$ represents an alkyl group having from 1 to 5 carbon atoms; $Y_1$ represents an alkyloxycarbonyl group having from 1 to 3 carbon atoms, a phenoxycarbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, an benzoyl group substituted by halogen atom(s), a 2-furanylcarbonyl group or an N,N-dimethylcarbamoyl group; and $Z_1$ represents =N—NO$_2$ or =N—CN.

The compounds of the formula (1E) can be produced with ease and in high yield by reacting a compound of the formula (10) with a compound of the formula (9).

The reaction is effected with ease in various solvents in the presence of a base.

The base to be used includes alkali metal hydroxides such as sodium hydroxide and potassium hydroxide, alkaline earth metal hydroxides such as magnesium hydroxide and calcium hydroxide, alkali metal hydrides such as sodium hydride and potassium hydride, alkali metal alcoholates such as sodium methylate and sodium ethylate, alkali metal oxides such as sodium oxide, carbonates such as potassium carbonate and sodium carbonate, phosphates such as tripotassium phosphate, trisodium phosphate, dipotassium hydrogenphosphate and disodium hydrogenphosphate, acetates such as sodium acetate and potassium acetate, organic bases such as pyridine, 4-(dimethylamino)pyridine, DBU, triethylamine and diazabicycloundecene, and the like.

The solvents to be used may include not only water but also alcohols such as methanol, ethanol, propanol and butanol, aromatic hydrocarbons such as benzene, toluene and xylene, aliphatic hydrocarbons such as hexane, heptane and petroleum benzine, aprotic polar solvents such as dimethylformamide, dimethylacetamide, dimethylsulfoxide, 1,3-dimethyl-2-imidazolidinone and 1-methyl- 2-pyrrolidinone, ethers such as ethyl ether, diisopropyl ether, 1,2-dimethoxyethane, tetrahydrofuran and dioxane, nitriles such as acetonitrile and propionitrile, ketones such as acetone and diisopropyl ketone, chlorinated solvents such as methylene chloride and chloroform, and the like.

The reaction temperature and the reaction time can be varied over wide ranges. In general, the reacation temperature is in the range of from $-20°$ to $200°$ C., preferably from $0°$ to $150°$ C., and the reaction time is in the range of from 0.01 to 50 hours, preferably from 0.1 to 15 hours.

The compound of the formula (10) in the reaction scheme (V) can be produced in accordance with the procedure of the reaction scheme (I) or (II).

The compound of the formula (9) in the reaction scheme (V) can be produced from known carboxylic acids in accordance with known methods for the production of acid chlorides.

Method (F):

The production of compounds of a formula (1F) where $R_1$ stands for a hydrogen atom, $R_2$ for $NHR_{11}$, and Z for =N—NO$_2$ is shown by a reaction scheme (VI).

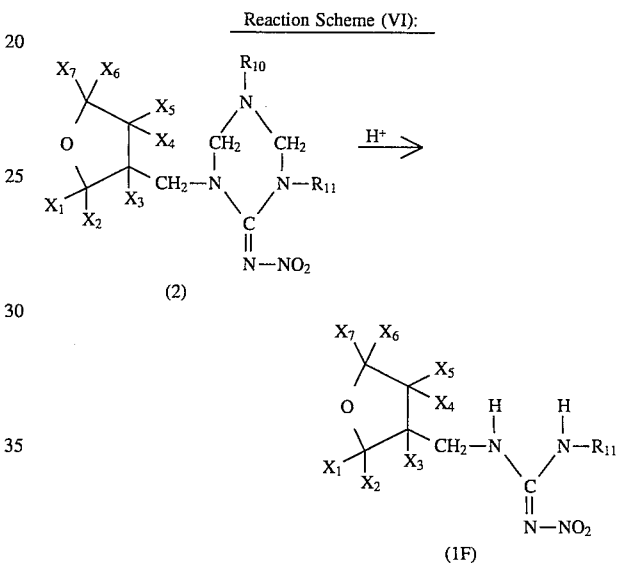

where $X_1$, $X_2$, $X_3$, $X_4$, $X_5$, $X_6$ and $X_7$ have the same meanings as described above; $R_{10}$ represents an alkyl group having from 1 to 5 carbon atoms or a benzyl group; and $R_{11}$ represents an alkyl group having from 1 to 5 carbon atoms or a benzyl group.

Namely, the compounds of the formula (1F) can be produced with ease and in high yield by treating a compound of the formula (2) under acidic conditions.

The reaction is effected with ease in various solvents in the presence of an acid or, if necessary, a catalyst.

The acid or catalyst to be used may include sulfonic acids such as p-toluenesulfonic acid and methanesulfonic acid, mineral acids such as sulfuric acid, hydrochloric acid and phosphoric acid, ion exchange resin, silica gel, zeolite, and the like. The solvents to be used may include not only water but also alcohols such as methanol, ethanol, propanol and butanol, aromatic hydrocarbons such as benzene, toluene and xylene, aliphatic hydrocarbons such as hexane, heptane and petroleum benzine, aprotic polar solvents such as dimethylformamide, dimethylacetamide, dimethylsulfoxide, 1,3-dimethyl-2-imidazolidinone and 1-methyl-2-pyrrolidinone, ethers such as ethyl ether, diisopropyl ether, 1,2-dimethoxyethane, tetrahydrofuran and dioxane, nitriles such as acetonitrile and propionitrile, ketones such as acetone and diisopropyl ketone, and the like.

The reaction temperature and the reaction time can be varied over wide ranges. In general, the reaction temperature is in the range of from −20° to 150° C., preferably from room temperature to 100° C.; and the reaction time is in the range of from 0.01 to 50 hours, preferably from 0.1 to 10 hours.

The compound of the formula (2) in the reaction scheme (VI) can be produced by the procedure of a reaction scheme (VIA):

Reaction Scheme (VIA):

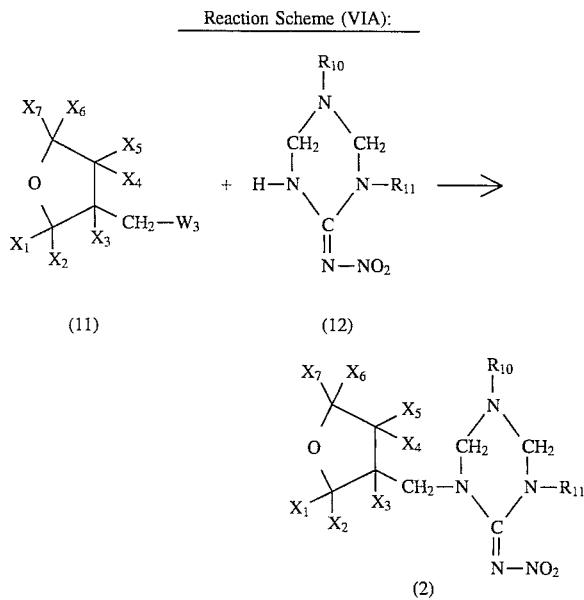

where $X_1$, $X_2$, $X_3$, $X_4$, $X_5$, $X_6$ and $X_7$ have the same meanings as described above; $W_3$ represents a chlorine atom, a bromine atom, a toluenesulfonyloxy group, a methanesulfonyloxy group or a trifluoromethanesulfonyloxy group; $R_{10}$ represents an alkyl group having from 1 to 5 carbon atoms or a benzyl group; and $R_{11}$ represents an alkyl group having from 1 to 5 carbon atoms or a benzyl group.

The compounds of the formula (2) can be produced with ease and in high yield by reacting a compound of the formula (11) with a compound of the formula (12).

The reaction is effected with ease in various solvents in the presence of a base or catalyst as occasion demands.

The base to be used includes alkali metal hydroxides such as sodium hydroxide and potassium hydroxide, alkaline earth metal hydroxide such as magnesium hydroxide and calcium hydroxide, alkali metal hydrides such as sodium hydride and potassium hydride, alkali metal alcoholates such as sodium methylate and sodium ethylate, alkali metal oxides such as sodium oxide, carbonates such as potassium carbonate and sodium carbonate, phosphates such as tripotassium phosphate, trisodium phosphate, dipotassium hydrogenphosphate and disodium hydrogenphosphate, acetates such as sodium acetate and potassium acetate, organic bases such as 4-(dimethylamino)pyridine, DBU, triethylamine and diazabicycloundecene, and the like.

The solvents to be used may include not only water but also alcohols such as methanol, ethanol, propanol and butanol, aromatic hydrocarbons such as benzene, toluene and xylene, aliphatic hydrocarbons such as hexane, heptane and petroleum benzine, aprotic polar solvents such as dimethylformamide, dimethylacetamide, dimethylsulfoxide, 1,3-dimethyl-2-imidazolidinone and 1-methyl- 2-pyrrolidinone, ethers such as ethyl ether, diisopropyl ether, 1,2-dimethoxyethane, tetrahydrofuran and dioxane, nitriles such as acetonitrile and propionitrile, ketones such as acetone and diisopropyl ketone, and the like.

The reaction temperature and the reaction time can be varied over wide ranges. In general, the reaction temperature is in the range of from −30° to 200° C., preferably from −20° to 150° C.; and the reaction time is in the range of from 0.01 to 50 hours, preferably from 0.1 to 15 hours.

The compound of the formula (11) in the reaction scheme (VIA) can be produced by-halogenating (tetrahydro-3-furanyl)methanol derivatives with a halogenating agent such as thionyl chloride, phosphorus oxychloride, phosphorus tribromide, triphenylphosphine/carbon tetrabromide and triphenylphosphine/carbon tetrachloride, or sulfonating the derivatives with a sulfonating agent such as tosyl chloride, methanesulfonyl chloride and trifluoromethanesulfonic acid anhydride.

The compound of the formula (12) in the reaction scheme (VIA) can be produced from a monoalkyl-substituted nitroguanidine or monobenzyl-substituted nitroguanidine, a primary amine and formaldehyde.

The compounds of the formula (1) may exist as isomers (cis- and trans-isomers) and tautomers. Further, since an asymmetric carbon atom is present at the 3rd position of the tetrahydrofuran ring, the compounds may exist as optically active isomers, racemic modifications, and mixtures thereof in optional proportions. Where the tetrahydrofuran ring has alkyl substituents, diastereomers may exist in some cases. These isomers can exist as mixtures in optional proportions. All of these isomers, tautomers and mixtures thereof are also included in the scope of the present invention.

The amine derivatives having a nitromethylene group, a nitroimino group or a cyanoimino group represented by the formula (1) according to the present invention are characterized by having a (tetrahydro-3furanyl)methyl group. For example, when the oxygen atom in the tetrahydrofuran ring is replaced by a sulfur atom or a nitrogen atom, the insecticidal activity of the derivatives is completely lost. It is also characteristics of the derivatives that the oxygen atom is present at the 3rd position. Tetrahydro-2-furylmethylamine derivatives, which has an oxygen atom at the 2nd position, show entirely no insecticidal activity. In other words, only (tetrahydro-3-furanyl)methylamine derivatives, which are saturated heterocyclic derivatives of a very limited structure, exhibit insecticidal activity very characteristically.

The derivatives of the formula (1) according to the invention have a powerful insecticidal activity and can be used as an insecticide in a variety of fields such as an agriculture, horticulture, livestock industry, forestry, forestry, disinfection and houses. The derivative of the formula (1) of the invention show exactly a high control effect on harmful insects without involving any phyto-toxicity to cultivated plants, higher animals and an environment.

Insect pest to which the derivatives of the formula (1) according to the invention can be applied, for instance, include:

LEPIDOPTERA

*Pseudaletia separata* Walker—rice armyworm
*Sesamia inferens* Walker—pink borer
Narangata aenescensMoore—green rice caterpillar
*Agrotis ipsilon* Hufnagel—black cutworm
*Anomis flava* Fabricius—cotton leaf caterpillar
*Helicoverpa armigera* Hubner—corn earworm
*Spodoptera exigua* Hubnet—beet armyworm
*Spodoptera litura* Fabricius—Common cutworm
*Agrotis segetum* Denis et Schiffermuller—cutworm
*Mamestra brassicae* Linnaeus—cabbage armyworm
*Autographa nigrisigna* Walker—beet semi-looper
*Chilo suppressalis* Walker—rice stem borer
*Cnaphalocrocis medinalis* Guenee—rice leafroller
*Scirpophaga incertulas* Walker—yellow rice borer
*Ectomyelois pyrivorella* Matsumura—pear fruit moth

*Hellulla undalis* Fabricius—cabbage webworm
*Maruca testulalis* Hubner—bean pod borer
*Parnara guttata* Bremer et Grey—rice skipper
*Pectinophora gossypiella* Saunders—pink bollworm
*Phthorimaea operculella* Zeller—potato tuberworm
*Pieris rapae crucivota* Boisduval—common cabbage worm
*Plodia interpunctella* Hubher—Indian meal worm
*Adoxophyes sp.*
*Phyllonorycter ringoniella* Matsumura—apple leafminer
*Phyllocnistis citrella* Stainton—citrus leafminer
*Eupoecillia ambiguella* Hubner—grape cochylid
*Graholita molesta* Busck—oriental fruit moth
*Leguminivora glycinivorella* Matsumara—soybean pod borer
*Carposina niponensis* Walsingham— peach fruit moth
*Paranthrene regalis* Butler—grape clearwing moth
*Caloptilia theivora* Walsingham—tea leafroller
*Plutella xylostella* Linnaeus—diamondback moth
*Tinea translucens* Meyrick—casemaking clothes moth
HEMIPTERA
*Bemisia tabaci* Gennadius—sweetpotato whitefly
*Trialeurodes vaporariorum* Westwood—greenhouse whitefly
*Aleurocanthus spiniferus* Quaintance—citrus spiny whitefly
*Aphis gossypii* Glover—cotton aphid
*Aphis citricola* van der Goot—spiraea aphid
*Eriosoma lanigerum* Hausmann—woolly apple aphid
*Myzus persicae* Sulzer—green peach aphid
*Brevicorvne brassicae* Linnaeus—cabbage aphid
*Lipaphis erysimi* Kaltenbach— turnip aphid
*Aphis craccivora* Koch—cowpea aphid
*Toxoptera aurantii* Boyer de Fonscolombe—black citrus aphid
*Toxoptera citricidus* Kirkaldy—tropical citrus aphid
*Viteus vitifolii* Fitch—grapeeleaf louse
*Schizaphis graminum* Rondani—greenbug
*Aulacorthum solani* Kaltenbach—foxglove aphid
*Empoasca onukii* Matsuda— tea green leaf hopper
*Arboridia apicalis* Nawa— grape leafhopper
*Laodelphax striatellus* Fallen— small brown planthopper
*Nilaparvata lugens* Stal— brown rice hopper
*Sogatella furcifera* Horvath— whitebacked rice planthopper
*Nephotettix cincticeps* Uhler— green rice leafhopper
*Nephotettix virescens* Distant— green rice leafhopper
*Cofana spectra* Distanrt— rice leafhopper
*Ceroplastes rubens* Maskell— red wax scale
*Saissetia oleae* Bernard— black scale
*Comstockaspis perniciosa* Comstock— San Jose scale
*Lepidosaphes ulmi* Linnaeus— oystershell scale
*Aonidiella aurantii* Maskell— California red scale
*Chrysomphalus ficus* Ashmead— Florida red scale
*Unaspis vanonensis* Kuwana— arrowhead scale
*Pseudococcus comstocki* Kuwana— Comstock mealybug
*Planococcus citri* Risso— citrus mealybug
*Icerya purchasi* Maskell— cottonycushion scale
*Pyslla mali* Schmidberger— apple sucker
*Diaphorina citri* Kuwayama— citrus psylla
*Nezara viridula* Linnaeus— southern green stink bug
*Riptortus clavatus* Thunberg— bean bug
*Stephanitis nashi* Esaki et Takeya— pear lace bug
COLEOPTERA
*Lissorhoptrus oryzophilus* Kuschhel— rice water weevil
*Oulema oryzae* Kuwayama— rice leaf beetle
*Phyllotreta striolata* Fabricius— striped flea beetle
*Leptinotarsa decemlineata* Say— Colorado potato beetle
*Chaetocnema concinna* Marshall
*Diabrotica spp*
*Sitophilus zeamais* Motschulsky—maize weevil
*Carpophilus hemipterus* Linnaeus—driedfruit beetle
*Epilachna vigintioctopunctata* Fabricius—twenty-eight-spotted ladybird
*Acanthoscelides obtectus* Say—bean weevil
*Callosobruchus chinensis* Linnaeus—adzuki bean weevil
*Callosobruchus maculatus* Fabricius—cowpea weevil
*Anomala cuprea* Hope—cupreous chafer
*Anomala rufocuprea* Motschulsky—soybean beetle
*Popilla japonica* Newman—japanese beetle
*Anoplophora malasiaca* Thomson—whitespotted longicom beetle
*Lasioderma serricorne* Fabicius—cigarette beetle
*Anthrenus verbasci* Linnaeus—varied carpet beetle
*Tribolium castaneum* Herbst—red flour beetle
*Lyctus brunneus* Stephens—powderpost beetle
HYMENOPTERA
*Culex piplens pallens* Coquilett
*Culex piplens molestus*
*Anopheles sinensis*
*Aedes albopictus*
*Agromyza oryzae* Munakata—rice leafminer
*Asphondylia sp.—soybean pod gall midge*
*Chlorops oryzae* Matsumura—rice stem maggot
*Hydrellia griseola* Fallen—rice leafminer
*Musca domestica vicina* Macquart—house fly
*Phormia regina* Meigen
*Delia antiqua* Meigen—onion maggot
*Dacus (Zeugodacus) cucurbitae* Coquillett—melon fly
*Dacus (Bactrocera) dorsalis* Hendel—oriental fruit fly
THYSANOPTERA
*Thrips tabaci* Lindeman—onion thrips
*Ponticulothrips diospyrosi* Haga et Okajima
*Thrips palmi* Karny
*Stenchaetothrips biformis* Bagnall—rice thrips
*Scirtothrips dorsalis* Hood—yellow tea thrips
ORTHOPTERA
*Periplaneta fuliginosa* Setville
*Periplaneta japonica* Karny
*Periplaneta americana* Linn—American cockroach
*Blattella germanica* Linne
*Oxya yezoensis* Shiraki—rice grasshopper
*Locusta migratoria* Linnaeus—Asiatic locust
HYMENOPTERA
*Athalia rosae ruficornis* Jakovlev—cabbage sawfly
ACARINA
*Tetranychus urticae* Koch—two-spotted spider mite
*Tetranychus kanzawai* Kishida—Kanzawa spider mite
*Panonychus ulmi* Koch—European red mite
*Polyphagotarsonemus latus* Branks—broad mite
*Aculops pelekassi* Keifer— pink citrus rust mite
*Eriophyes chibaensis* Kadono
*Ornithonyssus bacoti* Hirst
TROMBICULIDAE
*Tyrophagus putrescentiae* Schrank—dog flea
*Pediculus humanus humanus* De Geer
*Reticulitermes speratus* Kolbe
*Oxidus gracilis* C. L. Koch
*Thereuronema hilgendorfi* Verhoeff Where the compounds of the formula (1) of the invention are actually applied, they may be used singly without addition of any other ingredient. However, it is usual to incorporate carriers in order to make easier application as a control chemical.

For preparation of the compounds of the invention, any specific requirement is not necessary to formulate them into various preparations, such as emulsions, wettable powders, dusts, granules, fine powders, flowable preparations, microcapsules, oils, aerosols, smoking agents, poisonous feeds and the like, according to the procedures of preparing general agricultural chemicals well known in the art.

The term "carrier" used herein is intended to mean synthetic or natural, organic or inorganic materials which assist the effective ingredient to arrive at sites or portions to be treated and which are blended in order to make easier storage, transport and handling of the effective compound.

Appropriate solid carriers include, for example, inorganic substances such as montmorilonite, kaolinite, diatomaceous earth, white clay, talc, vermiculite, gypsum, calcium carbonate, silica gel and ammonium sulfate, and organic substances such as soybean flour, saw dust, wheat flour, pectin, methyl cellulose, sodium alginate, vaseline, lanolin, liquid paraffin, lard and vegetable oils.

Suitable liquid carriers include, for example, aromatic hydrocarbons such as toluene, xylene, cumene and solvent naphtha, paraffinic hydrocarbons such as kerosene and mineral oils, halogenated hydrocarbons such as methylene chloride, chloroform and carbon tetrachloride, ketones such as acetone, methyl ethyl ketone and cyclohexane, ethers such as dioxane, tetrahydrofuran, ethylene glycol monomethyl ether, ethylene glycol dimethyl ether, diethylene glycol monomethyl ether and propylene glycol monomethyt ether, esters such as ethyl acetate, butyl acetate and fatty acid glycerol ester, nitriles such as acetonitrile and propionitrile, alcohols such as methanol, ethanol, n-propanol, isopropanol and ethylene glycol, dimethylformamide, dimethylsulfoxide, water and the like.

In order to reinforce the efficacy of the compounds of the formula (1) of the invention, the following adjuvants may be used singly or in combination, depending on the type of preparation, the manner of application and the purpose.

Adjuvants used for the purpose of emulsification, dispersion, spreading, wetting, bonding and stabilization may include water-soluble bases such as ligninsulfonates, non-ionic surface active agents such as alkylbensenesulfonates, alkylsulfates, polyoxyethylene-alkyl aryl ethers and polyhydric alcohol esters, lubricants such as calcium stearate and waxes, stabilizers such as isopropyl hydrogenphosphate, methyl cellulose, carboxymethyl cellulose, casein, gum arabi, and the like. It should be noted that the adjuvants are not limited to those mentioned above.

The derivatives of the formula (1) according to the invention may develop better insecticidal activity when used in combination of two or more. If other physiologically active substances or chemicals are used in combination, multipurpose compositions with good efficacy can be prepared with the possibility of developing a synergistic effct.

Examples of such physiologically active substances include: synthetic pyrethroid insecticide or pyrethrum extracts, such as allethrin, tetramethrin, resmethrin, phenothrin, furamethrin, permethrin, cypermethrin, deltamethrin, cyhalothrin, cyfluthrin, fenpropathrin, tralomethrin, cycloprothrin, flucythrinate, fluvalinate, acrinathrin, tefluthrin, silafluofen, bifenthrin, empenthrin, beta-cyfluthrin, zeta-cypermethrin and the like; organo-phosphate insecticides such as DDVP, cyanophos, fenthion, fenitrothion, dichlofenthion, tetrachlorvinphos, dimethylvinphos, chlorfenvinphos, propaphos, methyparathion, temephos, phoxim, acephate, isofenphos, salithion, DEP,EPN, ethion, mecarbam, pyridafenthion, diazinon, pirimiphos-methyl, etrimfos, isoxathion, quinalphos, chloropyriphos-methyl, chloropyriphos, phosalone, phosmet, methidathion, oxydeprofos, vamidothion, malathion, phenthoate, dimethoate, fomothion, thiomelon, ethylthiometon, phorate, terbufos, oxydeprofos, profenophos, prothiofos, sulprofos, pyraclofos, monocrotophos, naled, fosthiazate and the like; carbamate insectiscides such as NAC, MTMC, MIPC, BPMC, XMC, PHC, MPHC, ethiofencarb, bendiocarb, primicarb, carbosurfan, benfuracarb, methomyl, oxamyl, aldicarb and the like: aryl propyl ether insecticides such as etofenprox, flufenprox, halfenprox and the like: aromatic alkane insecticides such as 1-(3-phenoxyphenyl)-4-(4-ethoxyphenyl)-4-methylpentane, 1-(3-phenoxy-4-fluorophenyl)- 4-(4-ethoxyphenyl)-4-methylpentan and the like; silyl ether insecticides such as silafluofen and the like: insecticidal natural substances such as nicotine-sulfate, polynactins, avermectin, milbemectin and the like; insecticides such as cartap, thiocyclam, bensultap, diflubenzuron, chlorfluazuron, teflubenzuron, triflumuron, flufenoxuron, novaluron, flucycloxuron, hexaflumuron, fluazuron, imidacloprid, nitenpyram, NI-25, pymetrozine, fipronil, buprofezin, fenoxycarb, pyriproxyfen, methoprene, hydroprene, kinoprene, endosulfan, diafenthiuron, triazuron. tebufenozide and the like; acaricides such as dicofol, CPCBS, BPPS, tetradifon, amitraz, benzoinate, fenothiocarb, hexythiazox, fenbutatin oxide, dienochlor, clofentezine, pyridaben, fenpyroximate, tebufenpyrad, pyrimidifen, agrimont and the like and other insecticides, acaricides, fungicides, nematocides, herbicides, plant regulators, fertilizers. soil improving materials, molting inhivitors, JH activators, BT agents, micro-organisms-derived toxins, natural or synthetic insect hormone disturbing agents, attractants, repellents, insect-pathogenic microorganisms, and small animals and other agricultural chemicals.

Although the compounds of the formula (1) of the invention are stable to light, heat and oxidation, antioxidants or UV absorbers may be added in appropriate amounts, if necessary, including, for example, phenol derivatives or bisphenol derivatives such as BHT (2,6-di-t-butyl-4-methylphenol), BHA (butylhydroxyanisole) and the like, arylamines or benzophenone compounds such as phenyl-α-naphthylamine, phenyl-β-naphthylamine, condensates of phenetidine and acetone, thereby obtaining more stable compositions.

The insecticide comprising the compound of the formula (1) of the invention contains the compound in an amount of from 0.0000001 to 95 wt.%, preferably from 0.0001 to 50 wt.%.

When the insecticide of the invention is applied, the effective ingredient is used generally at a concentration of from 0.001 to 5,000 ppm, preferably from 0.01 to 1,000 ppm. The application amount per 10 ares is generally in the range of from 1 to 300 g of the effective ingredient.

The present invention is more particularly described by way of the following examples and reference examples.

Example 1

Preparation of
1-[{(tetrahydro-3-furanyl)methyl}amino]-1-methyl-amino-2-nitroethylene (Compound No. 1):

A mixture comprising 7.0 g of (tetrahydro-3-furanyl)methylamine, 12.5 g of 1,1-bis(methylthio)-2-nitroethylene and 100 ml of acetonitrile was refluxed for 5 hours. The reaction mixture was concentrated under a reduced pressure, and purified by silica gel column chromatography (eluent :ethyl acetate/hexane=1/1) to give 6.6 g of 1-[{tetrahydro- 3-furanyl)methyl}amino]-1-methylthio- 2-nitroethylene. Then, a mixture comprising 4.0 g of the 1-[{(tetrahydro-3-furanyl)methyl}amino]-1-methylthio- 2-nitroethylene obtained above, 6.0 ml of 40% methylamine in methanol solution, 20 ml of 1N aqueous sodium hydroxide solution and 20 ml of ethanol was stirred at room temperature for 5 hours. The resulting reaction mixture was concentrated under a reduced pressure, and purified by silica gel column chromatography (eluent:ethyl acetate/methanol=9/1) to obtain 3.2 g of 1-[{(tetrahydro-3-furanyl)methyl}amino]-1-methylamino-2-nitroethylene.

Example 2

Preparation of
1-[{(tetrahydro-3-furanyl)methyl}amino]-
1-methylamino-2-nitroethylene (Compound No. 1):

A mixture comprising 1.79 g of 1-[{(tetrahydro-3-furanyl)methyl}amino-1-methylthio-2-nitroethylene, 1 ml of 40% methylamine in methanol solution and 30 ml of ethanol was stirred at room temperature for 5 hours. The reaction mixture was concentrated under a reduced pressure to give an oily matter. This was purified by column chromatography to obtain 1.54 g of 1-[{tetrahydro-3-furanyl)methyl}amino]-1-methylamino-2-nitroethylene.

Example 3

Preparation of
1-[{(tetrahydro-3furanyl)methyl}amino]-1-ethylamino-
2-nitroethylene (Compound No. 2):

A mixture comprising 0.51 g of 1-[{(tetrahydro-3-furanyl)methyl}amino]-1-methylthio-2-nitroethylene, 1 ml of 70% aqueous ethylamine solution and 10 ml of ethanol was stirred at room temperature for 5 hours. The reaction mixture was concentrated under a reduced pressure to give an oily matter. This was purified by column chromatography to obtain 0.50 g of 1-[{(tetrahydro-3-furanyl)methyl}amino] -1-ethylamino-2-nitroethylene.

Example 4

Preparation of
1-[{(tetrahydro-3-furanyl)methyl}amino]-1-dimethyl-
amino-2-nitroethylene (Compound No. 3):

A mixture comprising 4.0 g of 1-[{(tetrahydro-3-furanyl)methyl}amino]-1-methylthio-2-nitroethylene, 10 ml of 50% aqueous dimethylamine solution and 50 ml of acetonitrile was stirred at room temperature for an hour. The reaction mixture was concentrated under a reduced pressure, and purified by silica gel column chromatography (eluent:ethyl acetate/acetone=1/1) to obtain 2.8 g of 1-[{(tetrahydro-3-furanyl)methyl}amino]-1-dimethylamino- 2-nitroethylene.

Example 5

Preparation of
1-[{(tetrahydro-3-furanyl)methyl}amino]-1-(1-pyrrol-
idinyl)-2-nitroethylene (Compound No. 4):

A mixture comprising 1.2 g of 1-[{(tetrahydro-3-furanyl)methyl}amino]-1-methylthio-2-nitroethylene, 1.5 ml of pyrrolidine and 15 ml of acetonitrile was stirred at room temperature for an hour. The reaction mixture was concentrated under a reduced pressure, and purified by silica gel column chromatography (eluent:ethyl acetate/acetone= 1/1) to obtain 0.92 g of 1-[{(tetrahydro-3-furanyl)methyl}amino]-1-(1-pyrrolidinyl)- 2-nitroethylene.

Example 6

Preparation of
1-[N-{(tetrahydro-3-furanyl)methyl}-N-methylamino]-
1-methylamino-2nitroethylene (Compound No. 6):

A mixture comprising 1.42 g of (tetrahydro-3-furanyl)methyl tosylate, 0.15 g of sodium iodide, 1.70 g of potassium carbonate and 18 ml of 40% methylamine in methanol solution was heated under reflux for 5 hours. After separation of insoluble matters by filtration, the reaction fluid was concentrated under a reduced pressure to obtain crude N-{(tetrahydro-3-furanyl)methyl}-N-methylamine. To this were added 1.00 g of 1,1-bis(methylthio)- 2-nitroethylene and 14 ml of acetonitrile. The mixture was refluxed for 4 hours. The resultant reaction fluid was concentrated under a reduced pressure, and purified by silica gel column chromatography.(eluent:ethyl acetate/hexane=1/1) to obtain 1.00 g of 1-[N-{(tetrahydro-3-furanyl)methyl}-N-methylamino]-1-methylthio- 2-nitroethylene. A mixture comprising 0.9 g of the 1-[N-{(tetrahydro-3-furanyl)methyl}methylamino]-1-methylthio-2-nitroethylene obtained above and 15 ml of 40% methylamine in methanol solution was stirred for 45 minutes at room temperature. The reaction fluid was concentrated under a reduced pressure, and purified by silica gel column chromatography (eluent:ethyl acetate/methanol=3/1) to obtain 0.45 g of 1-[N-{(tetrahydro-3-furanyl)methyl}-N-methylamino]-1-methylamino- 2-nitroethylene.

Example 7

Preparation of
1-[N-{(tetrahydro-3-furanyl)methyl}-N-ethylamino]-
1-methylamino-2-nitroethylene (Compound No.
12):

A mixture comprising 4.09g of (tetrahydro-3-furanyl)methyl tosylate, 17 ml of 70% aqueous ethylamine solution and 8.2 ml of 2N aqueous sodium hydroxide solution was stirred at 75° C. for 6 hours. The reaction fluid was concentrated under a reduced pressure to obtain crude N-{(tetrahydro-3-furanyl)methyl}-N-ethylamine. To this were added 2.00 g of 1,1-bis(methylthio)-2-nitroethylene and 20 ml of acetonitrile. The resulting mixture was refluxed for 3 hours. The reaction fluid was concentrated under a reduced pressure, and purified by silica gel column chromatography (eluent:ethyl acetate/hexane=1/2) to obtain 0.81 g of 1-[N-{(tetrahydro- 3-furanyl)methyl}-N-ethylamino]-1-methylthio-2nitroethylene.

A mixture comprising 2.5 g of the 1-[N-{(tetrahydro-3-furanyl)methyl}-N-ethylamino]-1-methylthio-2-nitroethylene obtained above and 6 ml of 40% methylamine in methanol solution was stirred for 2 hours at room temperature. The reaction fluid was concentrated under a reduced pressure, and purified by silica gel column chromatography (eluent:ethyl acetate/methanol=7/1) to obtain 2.0 g of 1-[N-{(tetrahydro-3-furanyl)methyl}-N-ethylamino]- 1-methylamino-2-nitroethylene.

Example 8

Preparation of
1-[N-{(tetrahydro-3-furanyl)methyl}-N-propylamino]-
1-methylamino-2-nitroethylene (Compound No.
15):

A mixture comprising 3.00 g of (tetrahydro-3-furanyl)methyl tosylate, 0.20 g of sodium iodide, 3.50 g of potassium carbonate, 4.00 g of propylamine and 30 ml of ethanol was refluxed for 8 hours. After separation of insoluble matters by filtration, the reaction fluid was concentrated under a reduced pressure to obtain crude N-{(tetrahydro-3-furanyl)methyl}propylamine. To this were added 1.90 g of 1,1-bis(methylthio)-2-nitroethylene and 16 ml of acetonitrile. The resulting mixture was refluxed for 4 hours. The reaction fluid was concentrated under a reduced pressure, and purified by silica gel column chromatograpy (eluent:ethyl acetate/hexane=1/2) to obtain 1.00 g of 1-[N-{(tetrahydro-3-furanyl)methyl}-N-propylamino]-1-methylthio-2-nitroethylene. A mixture comprising 0.25 g of the 1-[N-{(tetrahydro-3-furanyl)methyl}-N-propylamino]- 1-methylthio-2-nitroethylene obtained above and 3 ml of 40% methylamine in methanol solution was stirred for 40 minutes at room temperature. The reaction fluid was concentrated under a reduced pressure, and purified by silica gel column chromatography (eluent:ethyl acetate/methanol=7/1) to obtain 0.22 g of 1-[N-{(tetrahydro-3-furanyl)methyl}propylamino]-1-methylamino- 2-nitroethylene.

Example 9

Preparation of 1-[N-{(tetrahydro-3-furanyl)methyl}-N-propylamino]-1-ethylamino-2-nitroethylene (Compound No. 16):

A mixture comprising 0.25 g of 1-[N-{(tetrahydro-3-furanyl)methyl}-N-propylamino]-1-methylthio-2-nitroethylene and 1 ml of 70% aqueous ethylamine solution was stirred for an hour at room temperature. After concentration of the mixture under a reduced pressure, the reaction fluid was purified by silica gel column chromatography (eluent: ethyl acetate/methanol=7/1) to obtain 0.25 g of 1-[N-{(tetrahydro-3-furanyl)methyl}-N-propylamino]-1-ethylamino-2-nitroethylene.

Example 10

Preparation of 1-{(tetrahydro-3-furanyl)methyl}-2-nitro-3-methylguanidine (Compound No. 20):

A mixture comprising 10.0 g of (tetrahydro-3-furanyl)methanol, 29.5 g of trifluoromethanesulfonic anhydride, 10.0 g of pyridine and 200 ml of dichloromethane was stirred for an hour at room temperature. Water was poured into the reaction solution to separate the organic layer, which was washed with 1N hydrochloric acid, water and a saturated saline solution, dried, and concentrated to obtain 20 g of 3-tetrahydro-furanylmethyl triflate. 3.25 g of 60% sodium hydride were added to 12.5 g of 1,5-dimethyl-2-nitroimino-hexahydro-1,3,5-triazine and 60 ml of DMF at room temperature, followed by stirring for an hour. 20.0 g of the 3-tetrahydrofuranylmethyl triflate were added thereto, and the mixture was stirred at 50° C. for 2 hours. After cooling the mixture to room temperature, 50 ml of 2N hydrochloric acid were added thereto, followed by stirring at 50° C. for 2 hours. The resultant mixture was neutralized with sodium bicarbonate and extracted with dichloromethane, and the extract was dried and concentrated. The residue thus obtained was purified by silica gel column chromatography (eluent:ethyl acetate/hexane=1/1) to obtain 7.8 g of 1-{(tetrahydro-3-furanyl)methyl}-2-nitro- 3-methylguanidine.

Example 11

Preparation of N-{(tetrahydro-3-furanyl)methyl}-N-(methyl)-nitroguanidine (Compound No. 26):

A mixture comprising 0.71 g of (tetrahydro-3-furanyl)methyl tosylate, 0.08 g of sodium iodide, 0.85 g of potassium carbonate and 9 ml of 40% methylamine in methanol solution was refluxed for 5 hours. After separating insoluble matters by filtration, the reaction fluid was concentrated under a reduced pressure to obtain crude N-{(tetrahydro-3-furanyl)methyl)methylamine. To this were added 0.38 g of S-methyl-N-(nitro)isothiourea and 7 ml of acetonitrile, followed by refluxing for 5 hours. The reaction fluid was concentrated under a reduced pressure, and purified by silica gel column chromatography (eluent: ethyl acetate/hexane= 1/1) to obtain 0.10 g of N-{(tetrahydro-3-furanyl)methyl}-N-(methyl)nitroguanidine.

Example 12

Preparation of 1-{(tetrahydro-3-furanyl)methyl}-2-nitro-3-methylguanidine (Compound No. 20):

A mixture comprising 0.7 g of 1-{(tetrahydro- 3-furanyl)methyl}-2-(nitroimino)-3,5-dimethylhexahydro- 1,3,5-triazine, 5 ml of 1N hydrochloric acid and 5 ml of ethanol was stirred at 40° C. for an hour. The reaction fluid was concentrated under a reduced pressure and purified by column chromatography to obtain 0.4 g of 1-{(tetrahydro-3-furanyl)methyl}-2-nitro-3-methylguanidine.

Example 13

Preparation of 1-{(tetrahydro-3-furanyl)methyl}-1-ethyl-2-nitro-3-methylguanidine (Compound No. 29):

A mixture comprising 5.5 g of N-{(tetrahydro-3-furanyl)methyl}-N-ethylamine, 3.0 g of S-methyl-N-nitro-N'-methyisothiourea, 30 ml of ethanol and 0.5 g of DMAP was refluxed for 4 hours. Then, the reaction fluid was concentrated under a reduced pressure to obtain an oily matter, which was purified by column chromatography. 1.1 g of 1-{(tetrahydro-3-furanyl)methyl}- 1-ethyl-2-nitro-3-methylguanidine were obtained.

Example 14

Preparation of N-(tetrahydro-3-furanyl)methyl-N'-cyano(methylthio)-formamidine (Compound No. 50):

A mixture comprising 0.61 g of (tetrahydro-3-furanyl)methylamine, 1.10 g of 90% S,S'-dimethyl-N-cyanocarbonate and 10 ml of acetonitrile was refluxed for 5 hours. The reaction fluid was concentrated under a reduced pressure and purified by silica gel column chromatography (eluent: ethyl acetate/hexane=1/1) to obtain 0.40 g of N-(tetrahydro-3-furanyl)methyl-N'-cyano(methylthio)formamidine.

Example 15

Preparation of
N-cyano-N'-{(tetrahydro-3furanyl)methyl}acetamidine
(Compound No. 55):

A mixture comprising 0.6 g of (tetrahydro-3-furanyl)methylamine, 0.7 g of ethyl N-cyanoacetamidate and 10 ml of ethanol was stirred for 3 hours at room temperature. The reaction fluid was concentrated under a reduced pressure and purified by silica gel column chromatography (eluent: ethyl acetate) to obtain 0.40 g of N-cyano-N'-{(tetrahydro-3-furanyl)methyl}acetamidine.

Example 16

Preparation of
N-cyano-N'-{(tetrahydro-3-furanyl)methyl}-N-methylacetamidine (Compound No. 51):

A mixture comprising 1.0 g of N-{(tetrahydro-3-furanyl)methyl}-N-methylamine, 0.4 g of ethyl N-cyanoacetamidate and 10 ml of ethanol was stirred for 7 hours at room temperature. The reaction fluid was concentrated under a reduced pressure and purified by silica gel column chormatography (eluent: ethyl acetate) to obtain 0.38 g of N-cyano-N'-{(tetrahydro-3-furanyl)methyl}-N-methylacetamidine.

Example 17

Preparation of
N-[4-{(2-methyl)tetrahydrofuranyl}methyl]-N'-methyl-N''-nitroguanidine (Compound No. 58):

A solution of 2.91 g of trifluoromethanesulfonic anhydride in 10 ml of dichloromethane was added dropwise over 5 minutes under ice-cooling to a solution of 1.00 g of 2-methyl-4-hydroxymethyltetrahydrofuran and 1.05 g of triethylamine in 50 ml of dichloromethane. The reaction fluid was stirred under ice-cooling for 30 minutes and at room temperature for 5 hours. The reaction fluid was concentrated under a reduced pressure to obtain an oily matter. This was added as a solution in 5 ml of dimethylformamide at room temperature to a reaction mixture, which had been obtained by adding at room temperature a solution of 1.24 g of 1-methyl-2-nitroimino- 5-methyl-1,3,5-triazine in 5 ml of dimethylformamide to a suspension of 0.32 g of sodium hydride (60%) in 5 ml of dimethylformamide and stirring the mixture at 60° C. for 30 minutes, followed by stirring at 60° C. for 4 hours. 7.2 ml of hydrochloric acid (2M) was added to the resultant reaction fluid, followed by stirring at 60° C. for 3 hours. After cooling the reaction fluid to room temperature, ethyl acetate was added thereto. The resultant reaction fluid was washed with water, and the organic layer was dried over anhydrous magnesium sulfate. The organic layer was concentrated under a reduced pressure to obtain an oily matter, which was purified by silica gel column chromatography (eluent:ethyl acetate) to obtain 77 mg of N-[4-{(2-methyl)tetrahydrofuranyl}methyl]-N'-methyl-N''-nitroguanidine as a red-brown oily matter.

Example 18

Preparation of
N-[4-{2-methyl)tetrahydrofuranyl}methyl]-N'-methyl-N''-nitroguanidine (Compound No. 58):

A solution of 4.19 g of triethylamine in 5 ml of dichloromethane was added dropwise under ice-cooling over 10 minutes to a solution of 5.70 g of {4-(2-methyl)tetrahydrofurylmethyl}amine hydrochloride and 9.07 g of S-methyl-N-nitro-N'-phthaloylisothiourea in 45 ml of dichloromethane. After stirring the reaction fluid for 2 hours under ice-cooling, insoluble matters were separated by filtration and the filtrate was washed with an aqueous hydrochloric acid solution (1M) and a saturated saline solution. The organic layer was dried over anhydrous magnesium sulfate and concentrated under a reduced pressure to obtain an oily matter. This was purified by silica gel column chromatography (eluent:hexane/ethyl acetate=1/1) to obtain 7.04 g of S-methyl-N-{(4-(2-methyl)tetrahydrofurylmethyl}-N'-nitroisothiourea as a colorless oily matter. To a solution of 9.39 g of the S-methyl-N-{(4-(2-methyl)tetrahydrofurylmethyl}-N'-nitroisothiourea obtained in this manner in 30 ml of methanol were added 3.43 g of methyl amine (as 40% methanol solution) at room temperature, followed by stirring for 1.5 hours at room temperature. The reaction fluid was concentrated under a reduced pressure to obtain an oily matter, which was purified by silica gel column chromatography (eluent:ethyl acetate) to obtain 7.77 g of N-[4-{(2-methyl)tetrahydrofuranyl}methyl]-N'-methyl-N''-nitroguanidine as a colorless oily matter.

Example 19

Preparation of 1-{(tetrahydro-3-furanyl)methyl}-1,2-dicyclohexylcarbonyl-2-methyl-3-nitroguanidine (Compound No. 33):

0.6 g of 1-{(tetrahydro-3-furanyl)methyl}-2-methyl- 3-nitroguanidine, 0.3 g of sodium hydride and 10 ml of acetonitrile were stirred at room temperature until foaming does not occur. A solution of 0.7 g of cyclohexylcarbonyl chloride in 5 ml of acetonitrile was added thereto dropwise under ice-cooling, followed by stirring for 30 minutes at room temperature. The reaction fluid was filtrated and the filtrate was concentrated. The oily matter thus obtained was purified by a silica gel column (eluent:ethyl acetate/hexane=1/1) to obtain 0.87 g of 1-{(tetrahydro-3-furanyl)methyl}-1,2-dicyclohexylcarbonyl- 2-methyl-3-nitroguanidine.

Example 20

Preparation of
1-{(tetrahydro-3-furanyl)methyl}-1,2-diethylcarbonyl-2-methyl-3-nitroguanidine (Compound No. 35):

0.6 g of 1-{(tetrahydro-3-furanyl)methyl}-2-methyl- 3-nitroguanidine, 0.3 g of sodium hydride and 10 ml of acetonitrile were stirred at room temperature until foaming does not occur. A solution of 1.0 g of propionyl chloride in 5 ml of acetonitrile was added thereto dropwise under ice-cooling, followed by stirring for 30 minutes at room temperature. The reaction fluid was filtrated and the filtrate was concentrated. The oily matter thus obtained was purified by a silica gel column (eluent:ethyl acetate/hexane=1:1) to obtain 0.51 g of 1-{(tetrahydro-3-furanyl)methyl}-1,2-diethylcarbonyl-2-methyl- 3-nitroguanidine.

Example 21

Preparation of 1-{(tetrahydro-3-furanyl) methyl}-1,2-dimethoxycarbonyl-2-methyl-3-nitroguanidine (Compound No. 38):

1.0 g of 1-{(tetrahydro-3-furanyl)methyl}-2-methyl- 3-nitroguanidine, 0.5 g of sodium hydride and 10 ml of acetonitrile were stirred at room temperature until foaming does not occur. A solution of 1.5 ml of methyl chloroformate in 5 ml of acetonitrile was added thereto dropwise between −5° and 3° C., followed by stirring for 30 minutes at room temperature. The reaction fluid was filtrated and the filtrate was concentrated. The oily matter thus obtained was purified by a silica gel column (eluent:ethyl acetate/hexane=1/1) to obtain 1.22 g of 1-{(tetrahydro-3-furanyl)methyl}-1,2-dimethoxycarbonyl- 2-methyl-3-nitroguanidine.

Example 22

Preparation of 1-{(tetrahydro-3-furanyl)methyl}-1,2-dibenzoyl-2-methyl-3-nitroguanidine (Compound No. 40):

1.0 g of 1-{(tetrahydro-3-furanyl)methyl}-2-methyl- 3-nitroguanidine, 0.5 g of sodium hydride and 10 ml of dimethylformamide were stirred at room temperature until foaming does not occur, and 1 ml of benzoyl chloride was added thereto dropwise, followed by stirring for 30 minutes at room temperature. Water was poured into the reaction fluid, the aqueous solution was extracted with ethyl acetate, and the extract was washed with water, dried, and concentrated. The oily matter thus obtained was purified by a silica gel column (eluent:ethyl acetate/hexane=1/2) to obtain 0.15 g of 1-{(tetrahydro-3-furanyl)methyl}-1,2-dibenzoyl-2-methyl- 3-nitroguanidine.

Reference Example 1

Preparation of 1-{(tetrahydro-3-furanyl)methyl}-2-(nitroimino)-3,5-dimethylhexahydro-1,3,5-triazine (Compound No. 2):

A mixture comprising 3.00 g of 1-{(tetrahydro- 3-furanyl)methyl}-2-(nitroimino)-5-methylhexahydro- 1,3,5-triazine, 0.54 g of sodium hydride and 40 ml of DMF was stirred at 50° C. for 30 minutes. Then, 2.08 g of methyl iodide were added thereto, followed by stirring at 70° C. for 2 hours. The reaction fluid was poured into a saturated saline solution and the mixture was extracted with methylene chloride several times. The methylene chloride solution was dried over anhydrous sodium sulfate and concentrated under a reduced pressure. The crude oily matter thus obtained was purified by column chromatography to obtain 1.43 g of 1-{(tetrahydro-3-furanyl)methyl}- 2-(nitroimino)-3,5-dimethylhexahydro- 1,3,5-triazine.

Reference Example 2

Preparation of (tetrahydro-3-furanyl)methylamine (Compound No. B1):

1 ml of 25% aqueous NaOH solution was added to a suspension of 1.50 g of N-{(tetrahydro-3-furanyl)methyl}phthalimide in 8 ml of water, followed by stirring at 70° C. for 3 hours. The reaction fluid was added dropwise to an aqueous 10% HCl solution at 70° C. and the mixture was stirred for 5 hours at the same temperature. While the reaction fluid was hot, 12 ml of toluene was added thereto. The aqueous layer was separated, made weakly alkaline with an aqueous 50% NaOH solution, and extracted with dichloromethane. The extract was dried and concentrated under a reduced pressure to obtain 0.55 g of (tetrahydro-3-furanyl)methaylamine.

Reference Example 3

Preparation of {4-(2-methyl)tetrahydrofurylmethyl}amine hydrochloride (Compound No. B4):

(1) A solution of 14.1 g of methanesulfonyl chloride in 10 ml of tetrahydrofuran was added dropwise under ice-cooling over 30 minutes to a solution of 13.0 g of {4-(2-methyl)tetrahydrofuran}methanol and 12.5 g of triethylamine in 85 ml of tetrahydrofuran. The reaction fluid was stirred for an hour under ice-cooling and for 2 hours at room temperature. Then, insoluble matters were separated by filtration and the filtrate was concentrated under a reduced pressure to obtain an oily matter. A suspension of this oily matter and 20.7 g of potassium phthalimide in 115 ml of dimethylformamide was stirred at 80° C. for 3 hours. The reaction fluid was cooled to room temperature, to which ethyl acetate was added, and the mixture was washed with water. The organic layer was dried over anhydrous magnesium sulfate and concentrated under a reduced pressure to obtain an oily matter. This was purified by silica gel column chromatography (eluent:hexane/ethyl acetate=2/1) and recrystallization (from ethylacetate and hexane) to obtain 22.1 g of N-{4-(2-methyl)tetrahydrofurylmethyl}phthalimide as colorless crystals.

(2) A solution of 21.0 g of N-{4-(2-methyl)tetrahydrofurylmethyl}phthalimide and 4.86 g of hydrazine monohydrate (98%) in 100 ml of ethanol was refluxed for 2 hours. The reaction fluid was cooled to room temperature, to which 8.6 ml of concentrated hydrochloric acid were added, and the mixture was stirred for 1.5 hours at room temperature. Insoluble matters were separated by filtration and the filtrate was concentrated under a reduced pressure to remove ethanol. An aqueous sodium hydroxide solution was added to the resulting filtrate to make it alkaline. The aqueous solution thus obtained was extracted with dichloromethane, and the organic layer was dried over anhydrous potassium carbonate and concentrated under an atmospheric pressure to obtain an oily matter. 60 ml of ethyl acetate was added to the oily matter, followed by addition of 30 ml of a solution of hydrogen chloride in ethyl acetate (4M) under ice-cooling. The crystals thus precipitated out were separated by filtration to obtain 5.70 g of {4-(2-methyl)tetrahydrofurylmethyl}amine hydrochloride as colorless crystals.

Reference Example 4

Preparation of {2-methyl-(4-tetrahydrofuran)}methanol (Compound No. C1):

(1) A solution of 25.0 g of diethyl malonate in 5 ml of dimethylformamide was added dropwise under ice-cooling over 20 minutes to a suspension of 6.55 g of sodium hydride in 90 ml of dimethylformamide. The reaction fluid was stirred for an hour under ice-cooling, to which a solution of 17.3 g of chloroacetone in 5 ml of dimethylformamide was added, and the mixture was stirred for an hour under ice-cooling and for 6 hours at room temperature. Ethyl acetate was added to the reaction fluid and the mixture was washed with water. The organic layer was dried over anhydrous magnesium sulfate. An oily matter obtained by concentrating the organic layer under a reduced pressure was distilled under vacuum to obtain 14.8 g of diethyl 2-oxopropylmalonate as a yellow oily matter.

$\delta_{TMS}$CDCl$_3$(ppm): 1.27 (6H, t, J=7.3), 2.21 (3H, s), 3.06 (2H, d, J=7.3), 3.86 (1H, t, J=7.3), 4.20 (4H, q, J=7.3) $v_{MAX}$, neat(cm$^{-1}$): 2985, 2940, 1732, 1467, 1448, 1406, 1370, 1332, 1273, 1237, 1161, 1098, 1050, 1026, 867 b.p.: 125°–135° C. (5 mmHg)

(2) A solution of 11.4 g of diethyl 2-oxopropylmalonate in 30 ml of tetrahydrofuran was added dropwise under ice-cooling over 20 minutes to a suspension of 5.00 g of lithium aluminum hydride in 100 ml of tetrahydrofuran. The reaction fluid was stirred for an hour under ice-cooling and for 4.5 hours at room temperature, and 10 ml of water was added thereto dropwise under ice-cooling over 20 minutes. The reaction fluid was refluxed for an hour and filtrated. The unfiltered solid was suspended in 200 ml of ethanol and the suspension was refluxed. The suspension was filtrated, and the filtrate combined with the foregoing filtrate was concentrated under a reduced pressure to obtain 7.08 g of 2-hydroxymethyl-1,4-pentanediol as a colorless oily matter.

$v_{MAX}$, neat (cm$^{-1}$): 3313, 2969, 2928, 1706, 1457, 1420, 1375, 1091, 1050

(3) A mixture comprising 7.08 g of 2-hydroxy-methyl-1,4-pentanediol and 7.3 ml of phosphoric acid (85%) was stirred at 120° C. for 3 hours. The reaction mixture was cooled to room temperature, to which water was added, and the mixture was extracted with dichloromethane. The organic layer was dried over anhydrous magnesium sulfate and concentrated under a reduced pressure. An oily matter thus obtained was distilled under vacuum to obtain 2.69 g of {2-methyl-(4-tetrahydrofuran)m}ethanol as a colorless oily matter.

Reference Example 5

Preparation of
N-{(tetrahydro-3furanyl)methyl}phthalimide
(Compound No. D4):

A mixture comprising 30.0 g of (tetrahydro-3-furanyl)methyl tosylate, 23.0 g of potassium phthalimide and 150 ml of DMF was stirred at 80° C. for 8 hours. Water was poured into the reaction mixture, and crystals precipitated out was separated by filtration to obtain 27.0 g of N-{(tetrahydro-3-furanyl)methyl}phthalimide.

Reference Example 6

Preparation of (tetrahydro-3-furanyl)methyl tosylate
(Compound No. D5):

A mixture comprising 50 g of (tetrahydro-3-furanyl)methanol, 95 g of tosyl chloride, 52 g of triethylamine and 450 ml of THF was refluxed for 8 hours. After separation of insolubles by filtration, the reaction fluid was concentrated under a reduced pressure, and the residue was purified by silica gel column chromatography (eluent:ethyl acetate/hexane=1/7) to obtain 114.5 g of (tetrahydro-3-furanyl)methyl tosylate.

Reference Example 7

Preparation of (tetrahydro-3-furanyl)methyl
bromide (Compound No. D6):

To a mixture comprising 10 g of phosphorus tribromide, 0.8 g of pyridine and 100 ml of ether were added dropwise 10 g of (tetrahydro-3-furanyl)methanol over 30 minutes. The resulting mixture was stirred for 5.5 hours. The reaction fluid was concentrated under a reduced pressure, and the residue was purified by silica gel column chromatography (eluent: ethyl acetate/hexane=1/1) to obtain 8.6 g of (tetrahydro-3-furanyl)methyl bromide.

Specific examples of the compounds of the formula (1) prepared in accordance with the same procedures as described in Examples 1 through 22 and Reference Examples 1 through 7 and examples of intermediates thereof are illustrated in Tables 1–4 along with the compounds of the Examples and Reference Examples.

TABLE 1

| Compound No. R$_1$ R$_2$ | Physical Properties |
|---|---|
| | (Z=CH—NO$_2$, X$_1$=X$_2$=X$_3$=X$_4$=X$_5$=X$_6$=X$_7$=H in formula (1)) |
| 1<br>H<br>NHMe | $\delta_{TMS}$(DMSO-d$_6$)(ppm):1.51–1.63(1H, m),<br>1.90–2.04(1H, m)<br>2.42–2.54(1H, m), 2.67–2.91(3H, br), 3.05–3.25(2H, br)<br>3.40–3.47(1H, br), 3.59–3.81(3H, br),<br>6.45–6.55(1H, br)<br>7.15–7.28(1H, br), 9.90–10.1(1H, br)<br>$v_{max}$(KBr)(cm$^{-1}$):3186, 1637, 1584, 1222, 997<br>m.p.:140.0–141.0°C. |
| 2<br>H<br>NHEt | $\delta_{TMS}$(CDCl$_3$)(ppm):1.21–1.41(3H, m),<br>1.65–1.82(1H, m)<br>2.05–2.25(1H, m), 2.50–2.71(1H, m), 3.02–3.35(4H, m)<br>3.55–4.01(4H, m), 5.41–5.82(1H, br), 6.58(1H, s),<br>10.00–10.90(1H, br)<br>$v_{max}$(neat)(cm$^{-1}$):3274, 1615, 1233<br>n$_D$(18.4°C.):1.5455 |
| 3<br>H<br>NMe$_2$ | $\delta_{TMS}$(CDCl$_3$)(ppm):1.57–1.69(1H, m),<br>2.11–2.29(1H, m)<br>2.45–2.67(1H, m), 2.94(6H, s), 3.19–3.35(2H, m),<br>3.56(1H, dd, J=5.2Hz, J=8.8Hz), 3.70–3.99(3H, m),<br>6.51(1H, s)<br>9.63(1H, br)<br>$v_{max}$(neat)(cm$^{-1}$):3261, 1615, 1515, 1435, 1271 |
| 4<br>H<br>pyrolidinyl | $\delta_{TMS}$(CDCl$_3$)(ppm):1.60–1.72(1H, m),<br>1.96–2.01(4H, m)<br>2.12–2.24(1H, m), 2.51–2.67(1H, m), 3.26–3.37(2H, m)<br>3.41–3.46(4H, m), 3.59(1H, dd, J=5.2Hz, J=8.8Hz),<br>3.71–3.95(3H, m), 6.60(1H, s), 10.18(1H, br)<br>$v_{max}$(neat)(cm$^{-1}$):3267, 1597, 1457, 1270, 1235 |
| 5<br>Me<br>H | $\delta_{TMS}$(CDCl$_3$)(ppm):1.52–1.65(1H, m),<br>2.01–2.14(1H, m)<br>2.58–2.79(1H, m), 2.88(3H, s), 3.33(2H, d, J=7.3Hz),<br>3.49–3.54(1H, m), 3.73–3.83(2H, m), 3.89–3.97(1H, m),<br>6.63(1H, d, J=10.3Hz), 8.14(1H, d, J=10.3Hz)<br>$v_{max}$(neat)(cm$^{-1}$):1624, 1302, 1252 |
| 6<br>Me<br>NHMe | $\delta_{TMS}$(CDCl$_3$)(ppm):1.48–1.58(1H, m),<br>2.01–2.12(1H, m)<br>2.61–2.70(1H, m), 2.93(3H, s), 3.01(3H, d, J=5.1Hz),<br>3.20(2H, dd, J=1.5Hz, J=8.8Hz),<br>3.48(1H, dd, J=5.1Hz, J=8.8Hz)<br>3.71–3.82(2H, m), 3.89(1H, dt, J=5.1Hz, J=8.8Hz),<br>6.53(1H, s), 9.73(1H, br)<br>$v_{max}$(neat)(cm$^{-1}$):3420, 1616, 1437, 1220<br>n$_D$(21.4°C.):1.5698 |
| 7<br>H<br>N(Me)Bu-n | $\delta_{TMS}$(CDCl$_3$, ppm):1.26(3H, t, J=7.3),<br>1.25–1.35(2H, m)<br>1.55–1.68(3H, m), 2.04–2.17(1H, m), 2.50–2.64(1H, m),<br>2.89(3H, s), 3.15–3.28(2H, m), 3.38(2H, t, J=7.3),<br>3.56(1H, dd, J=5.1, J=8.8), 3.70–3.94(3H, m),<br>6.53(1H, s), 9.71(1H, br.)<br>$v_{max}$(neat, cm$^{-1}$):3276, 1682, 1560, 1254 |
| 8<br>Me<br>NHPr-n | $\delta_{TMS}$(CDCl$_3$)(ppm):1.01(3H, t, J=7.3Hz),<br>1.47–1.59(1H, m)<br>1.65–1.78(2H, m), 1.98–2.10(1H, m),<br>2.65(1H, septet, J=6.6Hz), 2.92(3H, s),<br>3.18–3.26(4H, m), 3.49(1H, dd, J=5.1Hz, J=8.1Hz),<br>3.70–3.81(2H, m), 3.89(1H, dt, J=5.1Hz, J=8.1Hz)<br>6.52(1H, s), 9.60(1H, br) |

TABLE 1-continued

| Compound No. R₁ R₂ | Physical Properties |
|---|---|
| 9<br>Me<br>NHCH₂-<br>proparg-<br>yl | $\nu_{max}$(KBr)(cm⁻¹):3430, 1588, 1235<br>$\delta_{TMS}$(CDCl₃, ppm):1.50–1.62(1H, m),<br>1.95–2.12(1H, m)<br>2.38(1H, t, J=2.2Hz), 2.66(1H, septet, J=6.6Hz),<br>2.96(3H, s), 3.26(1H, dd, J=5.1Hz, J=8.1Hz),<br>3.49(1H, dd, J=5.1Hz, J=8.1Hz), 3.72–3.94(4H, m),<br>4.03(2H, dd, J=2.2Hz, J=6.6Hz)<br>6.51(1H, s), 9.57(1H, br.)<br>$\nu_{max}$(neat, cm⁻¹):3430, 2170, 1586, 1332, 1239<br>$n_D$(20.7°C.):1.5682 |
| 10<br>Me<br>NHCH₂-<br>CH₂OCH₃ | $\delta_{TMS}$(CDCl₃, ppm):1.46–1.60(1H, m),<br>1.99–2.07(1H, m), 2.57–2.67(1H, m), 2.92(3H, s),<br>3.20(2H, dd, J=3.7Hz, J=8.1Hz)<br>3.38–3.49(3H, m), 3.41(3H, s), 3.58(2H, t, J=5.1Hz),<br>3.71–3.82(2H, m), 3.88(1H, dt, J=5.1Hz, J=8.1Hz),<br>6.51(1H, s)<br>9.53(1H, br.)<br>$\nu_{max}$(neat, cm⁻¹):3261, 1587, 1251 |
| 11<br>Me<br>NMe₂ | $\delta_{TMS}$(CDCl₃, ppm):1.42–1.57(1H, m),<br>2.00–2.12(1H, m)<br>2.59–2.71(1H, m), 2.95(6H, s), 2.96(3H, s),<br>3.17–3.25(2H, m), 3.42(1H, dd, J=5.1, J=8.8),<br>3.68–3.87(3H, m), 6.34(1H, s)<br>$\nu_{max}$(neat, cm⁻¹):1524, 1403, 1256 |
| 12<br>Et<br>NHMe | $\delta_{TMS}$(CDCl₃)(ppm):1.20(3H, t, J=7.3Hz),<br>1.47–1.62(1H, m)<br>1.97–2.10(1H, m), 2.54–2.67(1H, m),<br>3.01(3H, d, J=5.1Hz)<br>3.05–3.17(2H, m), 3.25(2H, q, J=7.3Hz),<br>3.49(1H, dd, J=5.1Hz, J=8.1Hz),<br>3.69–3.79(2H, m), 3.89(1H, dt, J=5.1Hz, J=8.1Hz),<br>6.55(1H, s), 9.89(1H, br)<br>$\nu_{max}$(neat)(cm⁻¹):3422, 1602, 1517, 1236 |
| 13<br>Et<br>NHEt | $\delta_{TMS}$(CDCl₃)(ppm):1.19(3H, t, J=7.3Hz),<br>1.34(3H, t, J=7.3Hz), 1.47–1.59(1H, m),<br>1.97–2.09(1H, m), 2.62(1H, septet, J=6.6Hz),<br>3.08–3.17(2H, m), 3.20–3.36(4H, m),<br>3.48(1H, dd, J=5.1Hz, J=8.1Hz), 3.66–3.82(2H, m),<br>3.88(1H, dt, J=5.1Hz, J=8.1Hz), 6.53(1H, s),<br>9.69(1H, br)<br>$\nu_{max}$(neat)(cm⁻¹):3444, 1591, 1235 |
| 14<br>Et<br>NHPr-n | $\delta_{TMS}$(CDCl₃)(ppm):1.01(3H, t, J=7.3Hz),<br>1.19(3H, t, J=7.3Hz), 1.50–1.78(3H, m),<br>1.94–2.08(1H, m), 2.62(1H, septet, J=6.6Hz),<br>3.13(2H, dq, J=5.1Hz, J=7.3Hz), 3.20–3.31(4H, m)<br>3.48(1H, dd, J=5.1Hz, J=8.1Hz), 3.69–3.78(2H, m),<br>3.88(1H, dt, J=5.1Hz, J=8.1Hz), 6.54(1H, s),<br>9.76(1H, br)<br>$\nu_{max}$(KBr)(cm⁻¹):3430, 1589, 1223 |
| 15<br>Pr-n<br>NHMe | $\delta_{TMS}$(CDCl₃, ppm):0.91(3H, t, J=7.3Hz),<br>1.47–1.66(3H, m)<br>1.97–2.07(1H, m), 2.63(1H, septet, J=6.6Hz),<br>3.00(3H, d, J=5.1Hz, 3.11–3.18(4H, m),<br>3.48(1H, dd, J=5.1Hz, J=8.1Hz)<br>3.69–3.84(2H, m), 3.88(1H, dt, J=5.1Hz, J=8.8Hz),<br>6.55(1H, s), 9.88(1H, br)<br>$\nu_{max}$(neat)(cm⁻¹):3258, 1593, 1236 |
| 16<br>Pr-n<br>NHEt | $\delta_{TMS}$(CDCl₃)(ppm):0.90(3H, t, J=7.3Hz),<br>1.34(3H, t, J=7.3Hz), 1.49–1.68(3H, m),<br>1.96–2.08(1H, m), 2.63(1H, septet, J=6.6Hz),<br>3.10–3.19(4H, m), 3.31(2H.dq, J=5.1Hz, J=7.3Hz)<br>3.47(1H, dd, J=5.1Hz, J=8.1Hz),<br>3.73(2H, q, J=8.1Hz), 3.88(1H, dt, J=5.1Hz,<br>J=8.1Hz), 6.54(1H, s), 9.69(1H, br)<br>$\nu_{max}$(neat)(cm⁻¹):3447, 1590, 1231 |
| 17<br>Pr-n<br>SMe | $\delta_{TMS}$(CDCl₃)(ppm):0.92(3H, t, J=7.3Hz),<br>1.51–1.73(3H, m),<br>2.00–2.12(1H, m), 2.44(3H, s),<br>2.66(1H, septet, J=6.6Hz)<br>3.42–3.60(5H, m), 3.70–3.83(2H, m),<br>3.88(1H, dt, J=5.1Hz, J=8.1Hz), 6.79(1H, s)<br>$\nu_{max}$(neat)(cm⁻¹):1542, 1260 |
| 18<br>(CH₂)₃-<br>OMe | $\delta_{TMS}$(CDCl₃)(ppm):1.47–1.59(1H, m),<br>1.83(2H, quintet, J=6.6Hz), 1.98–2.11(1H, m),<br>2.59–2.70(1H, m), 2.80(3H, d, J=5.1Hz),<br>3.01(2H, d, J=6.6Hz), 3.16(1H, dd, J=3.7Hz,<br>J=8.1Hz), 3.31(3H, s), 3.31–3.43(3H, m),<br>3.48(1H, dd, J=5.1Hz, J=8.1Hz), 3.70–3.92(3H, m),<br>6.56(1H, s), 9.85(1H, br)<br>$\nu_{max}$(neat)(cm⁻¹):3421, 1637, 1205 |
| 19<br>(CH₂)₃-<br>OMe<br>SMe | $\delta_{TMS}$(CDCl₃)(ppm):1.53–1.62(1H, m),<br>1.87(2H, quintet, J=6.6Hz), 1.97–2.11(1H, m),<br>2.44(3H, s), 2.58–2.70(1H, m), 3.32(3H, s),<br>3.39(2H, t, J=6.6Hz), 3.43–3.53(3H, m),<br>3.63(2H, t, J=6.6Hz), 3.70–3.93(3H, m), 6.80(1H, s)<br>$\nu_{max}$(neat)(cm⁻¹):1542, 1270, 1114<br>(Z=N—NO₂,<br>X₁=X₂=X₃=X₄=X₅=X₆=X₇=H in formula (1)) |
| 20<br>H<br>NHMe | $\delta_{TMS}$(CDCl₃, ppm):1.62–1.74(1H, m),<br>2.09–2.22(1H, m)<br>2.59–2.79(1H, m), 2.96(3H, d, J=5.1Hz),<br>3.35(2H, t, J=5.1Hz), 3.66–3.80(3H, m),<br>3.92–4.08(1H, m)<br>$\nu_{max}$(KBr, cm⁻¹):3339, 3280, 1618, 1316, 1231, 1169<br>m.p.:99.5–100.7°C. |
| 21<br>H<br>N(Me)Bu-n | $\delta_{TMS}$(CDCl₃, ppm):0.95(3H, t, J=7.3),<br>1.22–1.42(2H, m),<br>1.58–1.77(3H, m), 2.07–2.18(1H, m), 2.50–2.62(1H, m),<br>3.05(3H, s), 3.29–3.46(4H, m), 3.65–3.77(3H, m),<br>3.94(1H, dt, J=5.1, J=8.1), 6.51(1H, br.)<br>$\nu_{max}$(neat, cm⁻¹):3285, 1626, 1307 |
| 22<br>H<br>NHOMe | $\delta_{TMS}$(CDCl₃)(ppm):1.59–1.72(1H, m),<br>2.06–2.18(1H, m)<br>2.56–2.72(1H, m), 3.40(2H, t, J=6.6Hz),<br>3.64(1H, dd, J=8.8Hz, J=4.4Hz), 3.70–3.97(3H, m),<br>3.88(3H, s), 6.10(1H, br), 10.71(1H, br)<br>$\nu_{max}$(neat, cm⁻¹):3293, 1602, 1525, 1433, 1215<br>m.p.:95–106°C.(dec.) |
| 23<br>H<br>N(Me)₂ | $\delta_{TMS}$(CDCl₃)(ppm):1.55–1.78(1H, m),<br>2.06–2.23(1H, m)<br>2.48–2.65(1H, m), 3.10(6H, s), 3.29–3.50(2H, m),<br>3.58–3.82(3H, m), 3.85–4.00(1H, m), 6.77(1H, br-s)<br>$\nu_{max}$(KBr, cm⁻¹):3274, 2940, 1637, 1387, 1075<br>m.p.:127.1–128.8°C. |
| 24<br>H<br>N(Me)-<br>(tetrahy-<br>dro-3-<br>furanyl)<br>methyl | $\delta_{TMS}$(CDCl₃)(ppm):1.56–1.71(2H, m),<br>2.01–2.18(2H, m)<br>2.48–2.68(2H, m), 3.07(3H, s), 3.20–3.47(3H, m),<br>3.60–4.01(9H, m), 6.21–6.83(1H, m)<br>$\nu_{max}$(neat, cm⁻¹):3276, 2941, 2869, 1623, 1396,<br>1288, 1074, 910 |
| 25<br>H<br>N(Me)-<br>benzyl | $\delta_{TMS}$(CDCl₃, ppm):1.48–1.70(1H, m),<br>1.94–2.17(1H, m)<br>2.41–2.68(1H, m),<br>3.02(3H, s), 3.20–3.97(6H, m), 4.62(2H, s),<br>6.72(1H, br-s), 7.21–7.41(5H, m)<br>$\nu_{max}$(neat, cm⁻¹):3283, 1623, 1396, 1297 |
| 26<br>Me<br>NH₂ | $\delta_{TMS}$(DMSO-d₆, ppm):1.47–1.60(1H, m),<br>1.85–1.96(1H, m)<br>2.51–2.62(1H, m), 2.97(3H, s), 3.33–3.51(3H, m),<br>3.58–3.71(2H, m), 3.77(1H, dt, J=5.1Hz, J=8.1Hz),<br>8.37(2H, br.)<br>$\nu_{max}$(neat, cm⁻¹):3367, 1623, 1577, 1270 |
| 27<br>Me<br>NMe₂ | $\delta_{TMS}$(CDCl₃, ppm):1.50–1.62(1H, m),<br>1.95–2.10(1H, m)<br>2.56–2.69(1H, m), 2.96(6H, s), 2.99(3H, s),<br>3.26–3.40(2H, m), 3.47(1H, dd, J=5.1, J=8.8),<br>3.70–4.02(3H, m)<br>$\nu_{max}$(neat, cm⁻¹):1439, 1244 |
| 28<br>Et<br>NH₂ | $\delta_{TMS}$(CDCl₃)(ppm):1.20(3H, t, J=7.3Hz),<br>1.55–1.71(1H, m)<br>1.97–2.08(1H, m), 2.58–2.70(1H, m),<br>3.32(1H, dd, J=8.1Hz, J=14.7Hz), 3.42–3.50(3H, m),<br>3.56(1H, dd, J=5.1Hz, J=8.1Hz), 3.71–3.83(2H, m),<br>3.93(1H, dt, J=5.1Hz, J=8.1Hz), 8.24(2H, br)<br>$\nu_{max}$(neat)(cm⁻¹):3385, 1616, 1575, 1263 |
| 29 | $\delta_{TMS}$(CDCl₃)(ppm):1.17(3H, t, J=7.3Hz), |

TABLE 1-continued

| Compound No. R₁ R₂ | Physical Properties |
|---|---|
| Et NHMe | 1.48–1.72(1H, m) 1.95–2.12(1H, m), 2.38–2.52(1H, m), 2.98(3H, d, J=5.1Hz) 3.21–3.39(2H, m), 3.52–3.92(6H, m) ν_max(KBr, cm⁻¹):3299, 1632, 1320, 1235 m.p.:118.5–125.0°C. |
| 30 CH₂CH=CH₂ NHMe | δ_TMS(CDCl₃, ppm):1.55–1.72(1H, m), 1.92–2.09(1H, m) 2.48–2.62(1H, m), 2.78(3H, m), 3.19(1H, dd, J=8.0, J=13.9) 3.45(1H, dd, J=7.3, J=13.9), 3.49–3.60(1H, m), 3.70–3.95(5H, m), 5.15–5.27(2H, m), 5.70–5.89(1H, m), 8.53(1H, br-s) ν_max(KBr, cm⁻¹):3338, 2935, 1624, 1541 semi-solid |
| 31 benzyl N(Me)-benzyl | δ_TMS(CDCl₃, ppm):1.38–1.56(1H, m), 1.71–1.96(1H, m) 2.08–2.33(1H, m), 2.63(3H*½, s), 2.65(3H*½, s), 2.73–2.82(1H, m), 2.94–3.04(1H, m), 3.30–3.44(1H, m), 3.64–3.79(3H, m), 4.27(1H, dd, J=15.4, J=3.7), 4.59(1H, d, J=15.4) 4.91(1H*½, d, J=14.7), 4.99(1H, s), 5.08(1H*½, d, J=14.7), 7.18–7.38(10H, m) ν_max(neat, cm⁻¹):1656, 1530, 1283, 1079 m.p.:70–74°C. |
| 32 CO-cyclopropyl N(Me)CO-cyclopropyl | δ_TMS(CDCl₃, ppm):0.98–1.07(4H, m), 1.14–1.23(4H, m) 1.60–1.75(2H, m), 1.81–1.92(1H, m), 2.01–2.14(1H, m), 2.73(1H, br), 3.24(3H, br-s), 3.53–3.58(1H, m), 3.71–3.94(5H, m) ν_max(neat, cm⁻¹):1698, 1557, 1284 oily |
| 33 CO-cyclohexyl N(Me)CO-cyclohexyl | δ_TMS(CDCl₃, ppm):1.13–1.34(6H, m), 1.42–1.92(15H, m) 2.00–2.13(1H, m), 2.34–2.48(1H, m), 2.57–2.75(2H, m), 3.19 3H, s), 3.49–3.65(3H, m), 3.71–3.93(3H, m) ν_max(neat, cm⁻¹):1704, 1558, 1451, 1287 |
| 34 COCH₃ N(Me)-COCH₃ | δ_TMS(CDCl₃, ppm):1.52–1.68(1H, m), 2.02–2.14(1H, m), 2.20(3H, s), 2.40(3H, s), 2.62–2.78(1H, m), 3.16(3H, s) 3.48–3.95(6H, m) ν_max(neat, cm⁻¹):1706, 1558, 1274 oily |
| 35 COC₂H₅ N(Me)-COC₂H₅ | δ_TMS(CDCl₃, ppm):1.11–1.26(6H, m), 1.54–1.73(1H, m) 2.00–2.15(1H, m), 2.33–2.80(5H, m), 3.17(3H, br-s), 3.47–3.94(6H, m) ν_max(neat, cm⁻¹):1709, 1558, 1461, 1374, 1285 |
| 36 COCH(CH₃)₂ N(Me)-COCH(Me)₂ | δ_TMS(CDCl₃, ppm):1.15–1.26(12H, m), 1.57–1.70(1H, m) 2.02–2.14(1H, m), 2.57–2.76(2H, m), 2.95–3.12(1H, m), 3.22(3H, s), 3.50–3.92(6H, m) ν_max(neat, cm⁻¹):1706, 1559, 1286, 1068 oily |
| 37 COCH=CH₂ NCO(Me)-CH=CH₂ | δ_TMS(CDCl₃, ppm):1.50–1.72(1H, m), 2.00–2.16(1H, m) 2.57–2.80(1H, m), 3.19(3H, s), 3.53–3.59(1H, m), 3.68–3.96(5H, m), 5.80–5.93(2H, m), 6.26–6.63(4H, m) ν_max(neat, cm⁻¹):1698, 1554, 1404, 1284 |
| 38 COOCH₃ N(Me)-COOCH₃ | δ_TMS(CDCl₃, ppm):1.49–1.69(1H, m), 2.07–2.18(1H, m) 2.60–2.83(1H, br), 3.10–3.36(4H, br), 3.47–3.62(2H, br) 3.81(3H, s), 3.84(3H, s), 3.71–3.94(3H, m) ν_max(KBr, cm⁻¹):1690, 1542, 1263, 1057 |
| 39 H N(Me)-COO-benzyl | δ_TMS(CDCl₃, ppm):1.47–1.60(1H, m), 2.04–2.17(1H, m) 2.44–2.57(1H, m), 3.22–3.28(2H, m), 3.26(3H, s), 3.49(1H, dd, J=5.1, J=8.8), 3.78–3.82(1H, m), 3.88(1H, dt, J=5.1, J=8.8), 5.25(2H, m), 7.35–7.42(5H, m), 9.71(1H, br.) ν_max(neat, cm⁻¹):3215, 1733, 1606, 1260, 1163 |
| 40 | δ_TMS(CDCl₃, ppm):1.50–1.80(1H, m), |
| COphenyl N(Me)CO-phenyl | 1.87–2.03(1H, m) 2.51(3H, s), 2.57–2.70(1H, m), 3.03–3.12(1H, m), 3.19–3.27(1H, m), 3.37–3.54(1H, m), 3.64–3.90(3H, m), 7.43–7.75(10H, m) ν_max(KBr, cm⁻¹):1698, 1545, 1450, 1263 m.p.: 133–135°C.(dec.) |
| 41 CO(p-t-butylphenyl) N(Me)CO-(p-t-butylphenyl) | δ_TMS(CDCl₃, ppm):1.34(9H, s), 1.35(9H, s), 1.54–1.66(1H, m), 1.85–1.96(1H, m), 2.50(3H, s), 2.50–2.62(1H, m), 3.03(1H, dd, J=6.6, J=13.9), 3.18(1H, dd, J=8.1, J=13.9), 3.35–3.43(1H, m), 3.67–3.85(3H, m), 7.46–7.64(8H, m) ν_max(KBr, cm⁻¹):1696, 1542, 1267 m.p.:152.4–153.0°C. |
| 42 CO(p-Cl-Phenyl) N(Me)CO-(P-Cl-phenyl) | δ_TMS(CDCl₃, ppm):1.55–1.72(1H, m), 1.88–2.05(1H, m) 2.53–2.70(1H, m), 2.60(3H, s), 3.13–3.33(2H, m), 3.38–3.52(1H, m), 3.66–3.76(2H, m), 3.81–3.89(1H, m), 7.49(2H, d, J=8.1), 7.51(4H, s), 7.62(2H, d, J=8.1) ν_max(KBr, cm⁻¹):1692, 1550, 1444, 1267, 1092 m.p.:149°C.(dec.) |
| 43 CO-furyl N(Me)-COfuryl | δ_TMS(CDCl₃, ppm):1.64–1.80(1H, m), 1.93–2.10(1H, m) 2.66–2.87(1H, m), 3.16(3H, s), 3.51–3.60(1H, m), 3.71–3.93(5H, m), 6.55–6.60(2H, m), 7.23–7.27(2H, m), 7.60(2H, d, J=2.2) ν_max(KBr, cm⁻¹):1683, 1546, 1473, 1277, 1060 |
| 44 COMe NMe₂ | δ_TMS(CDCl₃, ppm):1.55–1.67(1H, m), 2.00–2.12(1H, m) 2.16(3H, s), 2.47–2.58(1H, m), 3.13(6H, br.s), 3.40–3.89(6H, m) ν_max(neat, cm⁻¹):1692, 1590, 1501, 1240 m.p.:89.0–89.7°C. |
| 45 COEt NMe₂ | δ_TMS(CDCl₃, ppm):1.19(3H, t, J=7.3), 1.54–1.67(1H, m) 1.97–2.09(1H, m), 2.17–2.58(3H, m), 3.08(3H, br.s), 3.18(3H, s), 3.43–3.55(1H, m), 3.67–3.90(4H, m) ν_max(neat, cm⁻¹):1685, 1589, 1508, 1247 |
| 46 CO-phenyl NMe₂ | δ_TMS(CDCl₃, ppm):1.64–1.77(1H, m), 2.00–2.13(1H, m) 2.55–2.76(1H, m), 3.53–3.62(1H, m), 3.74–3.95(5H, m), 7.36–7.78(5H, m) ν_max(neat, cm⁻¹):1681, 1499, 1255 |
| 47 CON(CH₃)₂ NHMe | δ_TMS(CDCl₃, ppm):1,55–1.68(1H, m), 2.00–2.18(1H, m) 2.42–2.64(1H, m), 2.81(6H*⅓, s), 3.02(6H*⅔, s), 3.02(6H*⅓, s), 3.19(6H*⅔, s), 3.25–3.32(2H, m), 3.50–3.57(1H, m), 3.71–3.93(3H, m), 8.99(1H, br) ν_max(neat, cm⁻¹):1683, 1589, 1489, 1385, 1254, 1124 oily |
| 48 Et N(Me)-COMe | δ_TMS(CDCl₃, ppm):1.20–1.34(3H, m), 1.55–1.70(1H, m) 2.04–2.17(1H, m), 2.17(3H, s), 2.55–2.85(1H., m), 3.11(3H, br.s), 3.25–3.60(4H, m), 3.70–3.95(4H, m) ν_max(neat, cm⁻¹):1695, 1564, 1506, 1256 |

(Z=N—CN, X₁=X₂=X₃=X₄=X₅=X₆=X₇=H in formula (1))

| Compound No. R₁ R₂ | Physical Properties |
|---|---|
| 49 H Me | δ_TMS(CDCl₃, ppm):1.55–1.66(1H, m), 2.04–2.14(1H, m) 2.34(3H, s), 2.51–2.62(1H, m), 3.36(2H, t, J=6.6Hz), 3.59(1H, dd, J=5.1Hz, J=8.8Hz), 3.69–3.81(2H, m), 3.92(1H, dt, J=5.1Hz, J=8.8Hz), 6.04(1H, br.) ν_max(KBr, cm⁻¹):3260, 2169, 1609, 1561 |
| 50 H SMe | δ_TMS(CDCl₃, ppm):1.61–1.74(1H, m), 2.06–2.19(1H, m) 2.50(3H, br.), 2.60(1H, br.), 3.38(2H, br.), 3.62–3.81(3H, m), 3.94(1H, dt, J=5.1Hz, J=8.1Hz), 6.30(1H*½, br.), 6.88(1H*½, br.) ν_max(KBr, cm⁻¹):3263, 2165, 1553 m.p.: 112.8–114.0°C. |
| 51 Me Me | δ_TMS(DMSO-d₆, ppm):1.50–1.60(1H, m), 1.88–2.00(1H, m) 2.35(3H*⅗, s), 2.36(3H*⅖, s), 2.50–2.62(1H, m), 2.97(⅖*3H, s), 3.10(⅗*3H, s), 3.35–3.55(3H, m), |

TABLE 1-continued

| Compound No. R₁ R₂ | Physical Properties |
|---|---|
| 52<br>Pr-n<br>NHMe | 3.58–3.74(3H, m)<br>ν_max(neat, cm⁻¹):2175, 1577<br>δ_TMS(CDCl₃, ppm):0.92(3H, t, J=7.3Hz),<br>1.54–1.67(3H, m)<br>2.00–2.10(1H, m), 2.54–2.68(1H, m),<br>3.15(3H, d, J=4.4Hz)<br>3.19–3.40(4H, m), 3.57(1H, dd, J=4.4Hz, J=8.8Hz),<br>3.68(1H, dd, J=5.9Hz, J=8.8Hz),<br>3.78(1H, dt, J=5.9Hz, J=8.1Hz),<br>3.93(1H, dt, J=5.9Hz, J=8.1Hz), 5.33(1H, br.)<br>ν_max(neat, cm⁻¹):3289, 2168, 1553, 1423<br>(Z=CH—NO₂, X₁=Me,<br>X₂=X₃=X₄=X₅=X₆=X₇=H in formula (1)) |
| 53<br>H<br>NHMe | δ_TMS(CDCl₃, ppm):1.26–1.33(3H, m),<br>1.64–1.76(1H, m)<br>2.14–2.30(2H, m), 2.88–2.96(3H, m), 3.20–3.26(2H, m),<br>3.71–3.98(3H, m), 6.59(1H, s), 10.23–10.33(1H, m)<br>ν_max(KBr, cm⁻¹):3277, 3212, 3096, 2968, 2872, 1626, 1595<br>1433, 1375, 1239, 1171, 1139, 1010, 867, 755, 735<br>m.p.:127.3°C.–127.9°C.<br>(Z=CH—NO₂, X₅=Me,<br>X₁=X₂=X₃=X₄=X₆=X₇=H in formula (1)) |
| 54<br>H<br>NHMe | δ_TMS(DMSO-d₆, ppm):1.00(3H, d, J=6.6Hz),<br>1.90–2.05(2H, m), 2.65–2.85(3H, br.),<br>3.15–3.45(3H, m), 3.75–3.90(3H, m)<br>6.47(1H, br.)<br>ν_max(KBr, cm⁻¹):3274, 1628, 1586, 1367, 1230, 1011<br>m.p.:127.5–129.0°C. |
| 55<br>Et<br>NHMe | δ_TMS(CDCl₃, ppm):1.00–1.10(3H, m),<br>1.19(3H, t, J=7.3Hz)<br>1.87–2.07(2H, m), 3.00(3H, d, J=5.1Hz),<br>3.20–4.02(8H, m)<br>6.54(1H, s), 9.88(1H, br.)<br>ν_max(neat, cm⁻¹):3422, 1597, 1236, 1019<br>(Z=N—NO₂, X₅=Me,<br>X₁=X₂=X₃=X₄=X₆=X₇=H in formula (1)) |
| 56<br>H<br>NHMe | δ_TMS(CDCl₃, ppm):1.11(3H, d, J=6.6),<br>2.01–2.14(2H, m)<br>2.96(3H, d, J=5.1), 3.28–3.38(3H, m),<br>3.67(1H, dd, J=4.4, J=8.8),<br>3.90(1H, dd, J=6.6, J=8.8), 4.07(1H, t, J=6.6)<br>ν_max(neat, cm⁻¹):3304, 1618, 1420, 1233<br>(Z=CH—NO₂, X₇=Me,<br>X₁=X₂=X₃=X₄=X₅=X₆=H in formula (1)) |
| 57<br>H<br>NHMe | δ_TMS(CDCl₃, ppm):1.12–1.30(3H, m),<br>1.63–1.90(1H, m)<br>2.19–2.29(1H, m), 2.64(1H, br.),<br>2.87(3H*½, d, J=4.4Hz)<br>3.00(3H*½, d, J=4.4Hz).3.19–3.45(2H, m),<br>3.68–4.13(3H, m), 6.60(1H, s), 10.20–10.25(1H, br.)<br>ν_max(KBr, cm⁻¹):3189, 2968, 1637, 1583, 1541, 1420, 1387<br>1222, 1171, 999, 750, 700<br>m.p.:114.0–120.5°C.<br>(Z=N—NO₂, X₇=Me,<br>X₁=X₂=X₃=X₄=X₅=X₆=H in formula (1)) |
| 58<br>H<br>NHMe | δ_TMS(CDCl₃, ppm):1.23(3H*⅔, d, J=6.6),<br>1.31(3H*⅓, d, J=5.9), 1.81–1.90(1H*⅓, m),<br>2.24–2.34(1H*⅓, m), 2.57–2.71(1H, m),<br>2.96(3H, d, J=5.1), 3.32–3.35(2H, m),<br>3.52–3.57(1H, m), 3.75–3.77(1H, m),<br>3.96–4.02(1H, m), 4.11–4.19(1H, m)<br>ν_max(neat, cm⁻¹):3305, 2967, 2934, 2869, 1618, 1561, 1419<br>1328, 1236, 1174, 1145, 787 |
| 59 | δ_TMS(CDCl₃, ppm):1.16–1.28(10H, m), |
| COC₂H₅<br>NCO(Me)-<br>C₂H₅ | 1.76–1.78(1H, m)<br>2.26–2.85(5H, m), 3.17(3H, brs), 3.45–4.15(5H, m)<br>ν_max(neat, cm⁻¹):2975, 2944, 2875, 1710, 1559, 1457, 1376<br>1286, 1208, 1179, 1106, 1059, 953, 887, 834, 816<br>(Z=CH—NO₂, X₅=X₇=Me,<br>X₁=X₂=X₃=X₄=X₆=H in formula (1)) |
| 60<br>H<br>NHMe | δ_TMS(CDCl₃, ppm):0.80–1.25(6H, m),<br>1.97–2.02(1H, m)<br>2.42–2.60(1H, m), 2.87–2.96(3H, m), 3.08–3.51(3H, m),<br>3.59–3.76(1H, m), 3.98–4.20(1H, m), 5.85(1H, br-s),<br>6.21(1H, br-s), 6.60(1H, s)<br>ν_max(neat, cm⁻¹):3262, 3191, 3062, 2968, 2932, 1637, 1579<br>1421, 1374, 1220, 1170, 997, 749 732, 687<br>m.p.:144.4°C.–145.1°C.<br>(Z=N—NO₂, X₅=X₇=Me,<br>X₁=X₂=X₃=X₄=X₆=H in formula (1)) |
| 61<br>H<br>NHMe | δ_TMS(CDCl₃, ppm):0.87–1.30(6H, m),<br>1.99–2.05(1H, m)<br>2.43–2.54(1H, m), 2.94–2.98(3H, m), 3.21–3.48(3H, m)<br>3.63–3.72(1H, m), 3.97–4.14(1H, m)<br>ν_max(neat, cm⁻¹):3309, 2970, 2934, 2878, 1716, 1617, 1569<br>1560, 1420, 1328, 1227, 1174, 1145, 1046, 864, 787<br>(Z=CH—NO₂, X₆=X₇=Me,<br>X₁=X₂=X₃=X₄=X₅=H in formula (1)) |
| 62<br>H<br>NHMe | δ_TMS(CDCl₃, ppm):1.22(3H, s), 1.33(3H, s),<br>1.44–1.51(1H, m), 2.02(1H, dd, J=12.5, J'=8.1),<br>2.69(1H, septet, J=7.3)<br>2.87(3H*½, d, J=4.4), 3.00(3H*½, d, J=4.4),<br>3.20–3.36(2H, m), 3.56–3.62(1H, m),<br>3.94–4.00(1H, m), 6.32(1H*½, br), 6.60(1H, s),<br>6.61(1H*½, br), 10.25(1H, br)<br>ν_max(KBr, cm⁻¹):3192, 2967, 1616, 1571, 1387, 1248,<br>1052 988, 926, 764<br>m.p.:132.0–133.1°C.<br>(Z=N—NO₂, X₆=X₇=Me,<br>X₁=X₂=X₃=X₄=X₅=H in formula (1)) |
| 63<br>H<br>SMe | δ_TMS(CDCl₃, ppm):1.23(3H, s),<br>1.34(3H, s), 1.47(1H, dd, J=13.2, J=7.3),<br>2.04(1H, dd, J=13.2, J=8.1), 2.53(3H, s),<br>2.72(1H, septet, J=7.3), 3.36–3.51(2H, m),<br>3.62(1H, dd, J=8.8, J=5.9), 4.00(1H, dd, J=8.8, J=6.6), 10.11(1H, br)<br>ν_max(KBr, cm⁻¹):3369, 2974, 1562, 1453, 1198, 1051, 794<br>m.p.:47.1–53.3°C. |
| 64<br>H<br>NHMe | δ_TMS(CDCl₃, ppm):1.22(3H, s), 1.33(3H, s),<br>1.43(1H, dd, J=12.5, J=7.3), 2.01(1H, dd, J=12.5,<br>J=8.1), 2.68(1H, septet, J=7.3), 2.97(3H, d, J=4.4),<br>3.35(1H, t, J=5.1), 3.62(1H, dd, J=8.8, J=5.1),<br>3.95(1H, dd, J=8.8, J=7.3)<br>ν_max(neat, cm⁻¹):3305, 2970, 1616, 1568, 1418, 1328, 1233<br>1173, 1047<br>(Z=N—NO₂, X₅=Et,<br>X₁=X₂=X₃=X₄=X₆=X₇=H in formula (1)) |
| 65<br>H<br>NHMe | δ_TMS(CDCl₃, ppm):1.07–1.14(3H, m),<br>1.96–2.20(2H, m)<br>2.45(3H, s), 3.32–3.72(4H, m), 3.94–4.06(2H, m),<br>6.58(1H, s), 10.6(1H, br.)<br>ν_max(neat, cm⁻¹):3420, 1562, 1341, 1233 |

TABLE 2

($X_1=X_2=X_3=X_4=X_5=X_6=X_7=H$ in formula (2))

| Compound No. $R_{11}$ $R_{10}$ | Physical Properties |
|---|---|
| A1<br>H<br>Me | $\delta_{TMS}$(CDCl$_3$, ppm): 1.61–1.71(1H, m), 2.01–2.11(1H, m)<br>2.67–2.72(1H, m), 2.63(3H, s), 3.41–3.60(2H, m), 3.78–3.95<br>(4H, m), 4.30(2H, s), 4.35(2H, s), 9.62(1H. br-s)<br>$v_{max}$(KBr, cm$^{-1}$): 3294, 2869, 1596, 1188<br>m.p.: 117.5–118.9° C. |
| A2<br>Me<br>Me | $\delta_{TMS}$(CDCl$_3$, ppm): 1.63–1.71(1H, m), 2.02–2.12(1H, m), 2.54<br>–2.63(1H, m), 2.67(3H, s), 3.05(3H, s), 3.26–3.93(6H, m)<br>4.29(2H, s), 4.32(2H, s)<br>$v_{max}$(neat, cm$^{-1}$): 3482, 2940, 2873, 1608, 1375, 1290 |
| A3<br>Et<br>Me | $\delta_{TMS}$(CDCl$_3$, ppm): 1.24(3H, t, J=7.3Hz), 1.58–1.71(1H, m)<br>1.99–2.19(1H, m), 2.59–2.62(1H, m), 2.67(3H, s), 3.31–3.57<br>(3H, m), 3.69–3.92(4H, m), 4.36(2H, s), 4.39(2H, s)<br>$v_{max}$(neat, cm$^{-1}$): 1613, 1325 |
| A4<br>CH$_2$—CH=CH$_2$<br>Me | $\delta_{TMS}$(CDCl$_3$, ppm): 1.54–1.70(1H, m), 2.01–2.13(1H, m)<br>2.54–2.62(1H, m), 2.64(3H, s), 3.26–3.94(6H, m), 4.01(2H,<br>d, J=6.6Hz), 4.27(2H, s), 4.34(2H, s), 5.28–5.37(2H, m)<br>5.77–5.92(1H, m)<br>$v_{max}$(neat, cm$^{-1}$): 2956, 1594, 1298 |
| A5<br>Me<br>Et | $\delta_{TMS}$(CDCl$_3$, ppm): 1.19(3H, t, J=7.3), 1.57–1.69(1H, m)<br>1.98–2.10(1H, m), 2.50–2.62(1H, m), 2.86(2H, q, J=7.3)<br>3.04(3H, s), 3.42(1H, dd, J=7.3, J=13.9), 3.48(1H, dd, J=<br>5.1, J=8.8), 3.61(1H, dd, J=7.3, J=13.9), 4.71–4.92(3H, m)<br>4.36(2H, s), 4.38(2H, s)<br>$v_{MAX}$(neat, cm$^{-1}$): 1606, 1379, 1273 |
| A6<br>Me<br>Pr-iso | $\delta_{TMS}$(CDCl$_3$, ppm): 1.19(6H, d, J=6.6), 1.56–1.67(1H, m)<br>1.98–2.11(1H, m), 2.53–2.65(1H, m), 3.04(3H, s), 3.18(1H,<br>septet, J=6.6), 3.33(1H, J=7.3, J=13.9), 3.49(1H, dd, J=<br>5.9, J=8.8), 3.61(1H, dd, J=7.3, J=13.9), 3.71–3.91(3H, m)<br>4.43(2H, s), 4.45(2H, s)<br>$v_{MAX}$(neat, cm$^{-1}$): 1609, 1386, 1272 |
| A7<br>Me<br>benzyl | $\delta_{TMS}$(CDCl$_3$, ppm): 1.59–1.69(1H, m), 1.99–2.10(1H, m)<br>2.46–2.58(1H, m), 3.03(3H, s), 3.32(1H, dd, J=7.3, J=13.9)<br>3.45(1H, dd, J=8.8, J=5.9), 3.60(1H, dd, J=8.1, J=13.9)<br>3.70–3.89(3H, m), 3.98(2H, s), 4.31(2H, s), 4.38(2H, s)<br>7.36–7.40(5H, m)<br>$v_{MAX}$(KBr, cm$^{-1}$): 1604, 1388, 1289<br>m.p.: 111–114° C. |

TABLE 3

($R_7=H$ in formula (5))

| Compound No. $X_1, X_2, X_3, X_4, X_5$ $X_6, X_7$ | Physical Properties |
|---|---|
| B1<br>$X_1=X_2=X_3=X_4=H$<br>$X_5=X_6=X_7=H$ | $\delta_{TMS}$(CDCl$_3$, ppm): 1.36(2H, br.), 1.52–1.64(1H, m), 1.98–<br>2.10(1H, m), 2.32(1H, septet, J=7.3Hz), 2.72(2H, d, J=<br>7.3Hz), 3.51(1H, dd, J=5.9Hz, J=8.8Hz), 3.75(1H, q, J=<br>7.3Hz), 3.82–3.91(2H, m)<br>$v_{MAX}$(neat, cm$^{-1}$): 3363, 1660, 1060 |
| B2<br>$X_1=X_2=X_3=X_4=H$<br>$X_5=$Me<br>$X_6=X_7=H$ | $\delta_{TMS}$(CDCl$_3$, ppm): 1.07(3H, d, J=6.6Hz), 1.46(2H, br.)<br>1.78–2.04(2H, m), 2.65(1H, dd, J=8.1Hz, J=12.5Hz), 2.85<br>(1H, dd, J=5.1Hz, J=8.1Hz), 3.32(1H, t, J=8.1Hz), 3.57(1H,<br>dd, J=6.6Hz, J=8.1Hz), 3.92–4.03(2H, m) |
| B3<br>$X_1=X_2=X_3=X_4=H$<br>$X_5=$Et<br>$X_6=X_7=H$ | $\delta_{TMS}$(CDCl$_3$, ppm): 0.92(3H, t, J=7.3), 1.29–1.42(1H, m)<br>1.47–1.56(3H, m), .1.71–1.95(2H, m), 2.66(1H, dd, J=8.8,<br>J=12.5), 2.83(1H, dd, J=5.1, J=12.5), 3.41(1H, dd, J=6.6, J=<br>8.8), 3.59(1H, dd, J=5.1, J=8.8), 3.91–4.00(2H, m) |
| B4<br>$X_1=X_2=X_3=X_4=H$<br>$X_5=X_6=H$<br>$X_7=$Me<br>Hydrochloric<br>acid salt | $\delta_{TMS}$(CDCl$_3$, ppm): 1.12(3H, s), 1.21(3H, s), 1.41(1H, dd,<br>J=12.5Hz, J=8.8Hz), 1.87–1.95(1H, m), 2.50–2.63(1H, m)<br>2.78(2H, d, J=7.3Hz), 3.48(1H, dd, J=8.8Hz, J=6.6Hz), 3.83<br>(1H, dd, J=8.8Hz, J=7.3Hz) |

TABLE 4

(formula (11))

| Compound No.<br>$X_1, X_2, X_3, X_4, X_5$<br>$X_6, X_7$<br>$W_3$ | Physical Properties |
|---|---|
| C1<br>$X_1=X_2=X_3=X_4=H$<br>$X_5=X_6=H$<br>$X_7=Me$<br>$W_3=OH$ | $\delta_{TMS}$(CDCl$_3$, ppm): 1.23(3H*½, d, J=5.9), 1.27(3H*½, d, J=5.9), 1.54–1.65(1H, m), 1.78–1.87(1H, m), 2.32(1H, br-s) 2.44–2.57(1H, m), 3.51–3.66(2H, m), 3.70–3.87(1H, m), 3.90 –4.11(2H, m)<br>b.p. (4mmHg): 70–74° C. |
| C2<br>$X_1=X_2=X_3=X_4=H$<br>$X_6=H$<br>$X_5=X_7=Me$<br>$W_3=OH$ | $\delta_{TMS}$(CDCl$_3$, ppm): 0.99(3H*½, d, J=7.3), 1.22(3H*½, d, J=7.3)1.84–2.10(3H, m), 3.52–3.63(2H, m), 3.67–3.76(2H, m), 4.00–4.08(1H, m) |
| C3<br>$X_1=X_2=X_3=X_4=H$<br>$X_5=H$<br>$X_6=X_7=Me$<br>$W_3=OH$ | $\delta_{TMS}$(CDCl$_3$, ppm): 1.22(3H, s), 1.30(3H, s), 1.43(1H, dd, J=12.5Hz, J=8.1Hz), 1.90(1H, dd, J=12.5Hz, J=8.1Hz), 2.54–2.68(1H, m), 2.63(1H, brs), 3.56–3.68(3H, m), 3.97(1H, t, J=8.1Hz) |
| D1<br>$X_1=X_2=X_3=X_4=H$<br>$X_5=X_6=H$<br>$X_7=Me$<br>$W_3=OSO_2CH_3$ | $\delta_{TMS}$(CDCl$_3$, ppm): 1.24(3H*⅖, d, J=5.9), 1.28(3H*⅗, d, J=5.9), 1.61–1.72(1H, m), 1.81–1.90(1H*⅗, m), 2.19–2.27 (1H*⅖, m), 2.66–2.79(1H, m), 3.02(3H, s), 3.53(1H*⅗, dd, J=9.5, 5.9), 3.78(1H*⅖, dd, J=9.5, 5.9), 4.03–4.25 (4H, m).<br>$\nu_{MAX}$(neat, cm$^{-1}$): 3355, 2974, 2938, 2873, 1717, 1457, 1355 1176, 1092, 1049, 977, 956, 831, 752 |
| D2<br>$X_1=X_2=X_3=X_4=H$<br>$X_5=X_6=H$<br>$X_7=Me$<br>$W_3=$<br>phthalimide | $\delta_{TMS}$(CDCl$_3$, ppm): 1.22(3H*⅗, d, J=5.9), 1.30(3H*⅖, d, J=5.9), 1.53–1.61(1H, m), 1.82–1.92(1H*⅗, m), 2.08–2.18 (1H*⅖, m), 2.72–2.86(1H, m), 3.54(1H*⅗, dd, J=6.6, 8.8) 3.63–3.84(3H+1H*⅖, m), 3.97–4.04(1H*⅗, m), 4.14–4.21 (1H*⅖, m), 7.71–7.90(4H, m) |
| D3<br>$X_1=X_2=X_3=X_4=H$<br>$X_6=H$<br>$X_5=X_7=Me$<br>$W_3=$<br>phthalimide | $\delta_{TMS}$(CDCl$_3$, ppm): 0.94–1.26(6H, m), 1.88–2.00(1H, m) 2.30–2.82(1H, m), 3.41–4.19(5H, m), 7.71–7.89(4H, m)<br>$\nu_{MAX}$(neat, cm$^{-1}$): 2975, 2937, 2849, 1768, 1709, 1608, 1467 1438, 1399, 1308, 1089, 1051, 909, 720<br>m.p.: 71.5° C.–72.3° C. |
| D4<br>$X_1=X_2=X_3=X_4=H$<br>$X_5=X_6=X_7=H$<br>$W_3=$<br>phthalimide | $\delta_{TMS}$(CDCl$_3$, ppm): 1.69–1.81(1H, m), 1.98–2.11(1H, m) 2.74(1H, septet, J=7.3Hz), 3.61(2H, dd, J=5.9Hz, J=8.1Hz) 3.65–3.88(4H, m), 3.95(1H, dt, J=5.9Hz, J=8.1Hz), 7.71– 7.80(2H, m), 7.84–7.78(2H, m)<br>$\nu_{MAX}$(neat, cm$^{-1}$): 1701, 1399, 1050, 719 |
| D5<br>$X_1=X_2=X_3=X_4=H$<br>$X_5=X_6=X_7=H$<br>$W_3=OSO_2$-tolyl | $\delta_{TMS}$(CDCl$_3$, ppm): 1.55(1H, m), 1.94–2.07 (1H, m), 2.46(3H, s), 2.59(1H, septet, J=6.6Hz), 3.49(1H, dd, J=5.1Hz, J=9.5Hz), 3.64–3.81(3H, m), 3.92(1H, t, J= 8.8Hz), 3.99(1H, dd, J=6.6Hz, J=9.5Hz), 7.36(2H, d. J= 8.1Hz), 7.79(2H, d, J=8.1Hz) |
| D6<br>$X_1=X_2=X_3=X_4=H$<br>$X_5=X_6=X_7=H$<br>$W_3=Br$ | $\delta_{TMS}$(CDCl$_3$, ppm): 1.62–1.76(1H, m), 2.05–2.16(1H, m) 2.70(1H, septet, J=7.3Hz), 3.40(2H, dd, J=1.5Hz, J=7.3Hz) 3.45–3.53(1H, m), 3.60(1H, dd, J=5.1Hz, J=8.8Hz), 3.80(1H, t, J=7.3Hz), 3.89–3.95(1H, m) |

In the same manner as in the preceding Example 1 to 22 and Reference example 1 to 7, comparative compound 1 to 3 and 5 which were used in Test example were prepared.

Comparative compound 1

1-{(tetrahydro-2-furanyl)methylamino}-1-methylamino-2-nitroethylene $\delta_{TMS}$ (CDCl$_3$, ppm): 1.62–1.75 (1H, m), 1.90–2.08 (3H, 2.82 (3H, d, J=5.0Hz), 3.27–3.37 (1H, m), 3.54–3.62 (1H, m), 3.77–3.93 (2H, m), 4.02–4.07 (1H, m), 6.58 (1H, s), 6.94 (1H, br), 10.27 (1H, br)

$\nu_{MAX}$ (KBr, cm$^{-1}$): 3265, 3200, 1622, 1584, 1375, 1225, 1010 m.p.: 136°–137.5° C.

Comparative compound 2

1-{(2-furylmethyl)amino}-1-methylamino-2-nitroethylene $\delta_{TMS}$ (DMSO-d$_6$, ppm): 2.67–2.92 (3H, br), 4.30–4.56 (2H, br), 6.36 (1H, d, J=2.9Hz), 6.42 (1H, d, J=2.9Hz), 6.45–6.57 (1H, br), 7.63 (1H, br), 9.94 (1H, br), 10.19 (1H, br)

$\nu_{MAX}$ (KBr, cm$^{-1}$): 3261, 1629, 1580, 1438, 1382, 1242 m.p.: 135.1°–136.5° C.

Comparative compound 3

1-tetrahydrofurfuryl-2-methyl-3-nitroguanidine $\delta_{TMS}$ (CDCl$_3$, ppm): 1.54–1.73 (1H, m), 1.87–2.20 (3H, m), 2.94 (3H, d, J=4.5Hz), 3.18–3.35 (1H, m), 3.54–3.71 (1H, m), 3.75–3.95 (2H, m), 4.01–4.15 (1H, m), 6.93 (1H, br), 9.41 (1H, br)

$\nu_{MAX}$ (neat)(cm$^{-1}$): 3300, 1640, 1561, 1307, 1205 m.p.: 79.5°–82.5° C.

Next, the insecticidal compositions of the present invention are more particularly described by way of the following formulation examples, in which all "part or parts" are "part or parts by weight".

Formulation Example 1

20 parts of the compound of the invention, 10 parts of Sorpol 355S (surfactant available from Toho Chem. Co.) and 70 parts of xylene were uniformly stirred and mixed to give an emulsion.

Formulation Example 2

10 parts of the compound of the invention, 2 parts of sodium alkylnaphthalenesulfonate, one part of sodium ligninsulfonate, 5 parts of white carbon and 82 parts of diatomaceous earth were uniformly stirred and mixed to give 100 parts of a wettable powder.

Formulation Example 3

0.3 part of the compound of the invention and 0.3 part of white carbon were uniformly mixed, and 99.2 parts of clay and 0.2 part of Driless A (available from Sankyo Co.) were added thereto and uniformly ground and mixed to give 100 parts of a powder preparation.

Formulation Example 4

2 parts of the compound of the invention, 2 parts of white carbon, 2 parts of sodium ligninsulfonate and 94 parts of bentonire were uniformly ground and mixed, and water was added thereto and kneaded, granulated and dried to give 100 parts of a granular preparation.

Formulation Example 5

20 parts of the compound of the invention and 5 parts of 20% aqueous solution of polyvinyl alcohol were fully stirred and mixed, and 75 parts of 0.8% aqueous solution of xanthane gum was added thereto and again stirred and mixed to give 100 parts of a flowable preparation.

Formulation Example 6

10 parts of the compound of the invention, 3 parts of carboxymethyl cellulose, 2 parts of sodium ligninsulfonate, one part of sodium dioctylsulfosuccinate and 84 parts of water were uniformly wet-ground to give 100 parts of a flowable preparation.

Next, explanation is made concretely by way of the following test examples to clarify the excellent insecticidal activity exhibited by the compounds of the formula (1) according to the invention.

Test Example 1

Effect on *Laodelphax striatellus* Fallen—smaller brown planthopper:

The compound of the invention was dissolved in acetone to a predetermined concentration, and 3 ml of the acetone solution was applied over a bundle of several rice seedlings (about third leaf stage). After drying in air, the treated seedling were covered with a metal gauze cylinder, in which ten female adults of smaller brown planthopper were released, followed by placing in a temperature controlled room at 25° C. After 48 hours, the mortality was checked. The results are shown in Table 5.

TABLE 5

Effect on *Laodelphax striatellus* Fallen - smaller brown planthopper

| Test Compound | Mortality (%) | |
|---|---|---|
| | 1000 ppm | 200 ppm |
| Nos. 1 | 100 | 100 |
| 2 | 100 | 70 |
| 3 | 100 | 100 |
| 6 | 100 | 100 |
| 7 | 100 | 100 |
| 8 | 100 | 50 |
| 11 | 100 | 100 |
| 12 | 100 | 100 |
| 13 | 100 | 100 |
| 15 | 100 | 100 |
| 18 | 100 | 100 |
| 20 | 100 | 100 |
| 23 | 100 | 100 |
| 25 | 100 | 100 |
| 27 | 100 | 100 |
| 29 | 100 | 100 |
| 31 | 100 | 100 |
| 32 | 100 | 100 |
| 33 | 100 | 100 |
| 34 | 100 | 100 |
| 35 | 100 | 100 |
| 36 | 100 | 100 |
| 37 | 100 | 100 |
| 38 | 100 | 100 |
| 39 | 100 | 100 |
| 40 | 100 | 100 |
| 41 | 100 | 70 |
| 42 | 100 | 70 |
| 43 | 100 | 100 |
| 44 | 100 | 100 |
| 45 | 100 | 100 |
| 46 | 100 | 70 |
| 47 | 100 | 100 |
| 48 | 100 | 100 |
| 54 | 100 | 100 |
| 55 | 100 | 100 |
| 56 | 100 | 100 |
| 57 | 100 | 100 |
| 58 | 100 | 100 |
| 59 | 100 | 100 |
| 60 | 100 | 100 |
| 61 | 100 | 100 |
| 62 | 100 | 100 |
| Comp. Compound (1) | 0 | 0 |
| Comp. Compound (2) | 0 | 0 |
| Comp. Compound (3) | 0 | 0 |
| Untreated | 0 | 0 |

Comparative Compound (1): 1-{(tetrahydro-2-furanyl)-methylamino}-1-methylamino-2-nitroethylene
Comparative Compound (2): 1-{(2-furylmethyl)amino}-1-methylamino-2-nitroethylene
Comparative Compound (3): 1-tetrahydrofurfuryl-2-methyl-3-nitroguanidine

Test Example 2

Effect on resistant strain of *Nepphotettix cincticeptus* Unler—resistant green rice leafhopper:

The compound of the invention was dissolved in acetone to a predetermined concentration and 3 ml of the acetone solution was applied over a bundle of several rice seedlings (about 3rd leaf stage). After drying in air, the treated seedlings were covered with a metal gauze cylinder, in which ten female adults of resistant green rice leafhopper were released, followed by placing in a temperature controlled room at 25° C. After 48 hours, the mortality was checked. The results are shown in Table 6.

TABLE 6

Effect on resistant strain of *Nephotettix cincticeptus* Uhler - resistant green rice leafhopper

| Test Compound | Mortality (%) | |
|---|---|---|
| | 1000 ppm | 200 ppm |
| Nos. 1 | 100 | 100 |
| 2 | 100 | 100 |
| 3 | 100 | 100 |
| 4 | 100 | 70 |
| 5 | 100 | 70 |
| 6 | 100 | 100 |
| 7 | 100 | 100 |
| 8 | 100 | 70 |
| 9 | 100 | 100 |
| 11 | 100 | 100 |
| 12 | 100 | 100 |
| 13 | 100 | 100 |
| 14 | 100 | 70 |
| 15 | 100 | 100 |
| 16 | 100 | 70 |
| 18 | 100 | 100 |
| 20 | 100 | 100 |
| 21 | 100 | 100 |
| 23 | 100 | 100 |
| 24 | 100 | 100 |
| 25 | 100 | 100 |
| 26 | 100 | 100 |
| 28 | 100 | 100 |
| 29 | 100 | 100 |
| 30 | 100 | 100 |
| 31 | 100 | 70 |
| 32 | 100 | 100 |
| 33 | 100 | 100 |
| 34 | 100 | 100 |
| 35 | 100 | 100 |
| 36 | 100 | 100 |
| 37 | 100 | 100 |
| 38 | 100 | 100 |
| 39 | 100 | 100 |
| 40 | 100 | 100 |
| 41 | 100 | 100 |
| 42 | 100 | 100 |
| 43 | 100 | 100 |
| 44 | 100 | 100 |
| 45 | 100 | 100 |
| 46 | 100 | 100 |
| 47 | 100 | 100 |
| 48 | 100 | 100 |
| 49 | 100 | 70 |
| 50 | 100 | 100 |
| 51 | 100 | 100 |
| 52 | 100 | 100 |
| 53 | 100 | 70 |
| 54 | 100 | 100 |
| 55 | 100 | 100 |
| 56 | 100 | 100 |
| 57 | 100 | 100 |
| 58 | 100 | 100 |
| 59 | 100 | 100 |
| 60 | 100 | 100 |
| 61 | 100 | 100 |
| 62 | 100 | 100 |
| 63 | 100 | 70 |
| 64 | 100 | 100 |
| Comp. Compound (1) | 0 | 0 |
| Comp. Compound (2) | 0 | 0 |
| Comp. Compound (3) | 0 | 0 |
| Untreated | 0 | 0 |

Comparative Compound (1): 1-{(tetrahydro-2-furanyl)-methylamino}-1-methylamino-2-nitroethylene
Comparative Compound (2): 1-{(2-furylmethyl)amino}-1-methylamino-2-nitroethylene
Comparative Compound (3): 1-tetrahydrofuryl-2-methyl-3-nitroguanidine

Test Example 3

Effect on *Spodoptera litura* Fabricius—Common cutworm

The emulsion of the compound of the invention prepared according to Formulation Example 1 was diluted with distilled water to a predetermined concentration, to which a spreading agent (New Gramin available from Sankyo Co.) was added at a concentration of 0.02%. Leaves of Ipomea batatas were immersed fully in the dilution. After drying in air, the leaves were transferred into a plastic cup with a diameter of 9 cm and a depth of 4 cm. Ten second-instar larvae of Common cutworm were place in the cup at 25° C. to eat the leaves. After 72 hours, the mortality was checked. The results are shown in Table 7.

TABLE 7

Effect on *Spodoptera litura* Fabricus - Common cutworm

| Test Compound | Mortality (%) | |
|---|---|---|
| | 1000 ppm | 500 ppm |
| Nos. 1 | 100 | 100 |
| 20 | 100 | 100 |
| 23 | 100 | 100 |
| 25 | 100 | 80 |
| 32 | 100 | 60 |
| 33 | 100 | 80 |
| 34 | 100 | 80 |
| 35 | 100 | 100 |
| 36 | 100 | 80 |
| 37 | 100 | 70 |
| 39 | 100 | 80 |
| 41 | 100 | 60 |
| 42 | 100 | 100 |
| 43 | 100 | 80 |
| 44 | 100 | 60 |
| 45 | 100 | 60 |
| 57 | 100 | 80 |
| 59 | 100 | 60 |
| Comp. Compound (1) | 0 | 0 |
| Comp. Compound (2) | 0 | 0 |
| Comp. Compound (3) | 0 | 0 |
| Untreated | 0 | 0 |

Comparative Compound (1): 1-{(tetrahydro-2-furanyl)-methylamino}-1-methylamino-2-nitroethylene
Comparative Compound (2): 1-{(2-furylmethyl)amino}-1-methylamino-2-nitroethylene
Comparative Compound (3): 1-tetrahydrofuryl-2-methyl-3-nitroguanidine

Test Example 4

Effect on *Myzus persicae* Sulzer—Green peach aphid:

The emulsion of the compound of the invention prepared according to formulation Example 1 was diluted with distilled water to a predetermined concentration, to which a spreading agent (New Gramin available from Sankyo Co.) was added at a concentration of 0.02%. The dilution thus prepared was sprayed over eggplant seedlings of 2nd or 3rd leaf stage, on which green peach aphids had been parasitic. The seedlings were grown in a green house. After 48 hours, the number of living aphids was compared to determine the mortality. The results are shown in Table 8.

TABLE 8

Effect on *Myzus persical* Suezer - green peach aphid

| Test Compound | Mortality (%) 100 ppm | 10 ppm |
|---|---|---|
| Nos. 1 | 100 | 50 |
| 6 | 100 | 100 |
| 13 | 100 | 56 |
| 15 | 100 | 51 |
| 18 | 100 | 45 |
| 20 | 100 | 100 |
| 32 | 99 | 40 |
| 33 | 100 | 72 |
| 34 | 100 | 60 |
| 35 | 100 | 77 |
| 36 | 100 | 73 |
| 39 | 94 | 34 |
| 40 | 97 | 41 |
| 44 | 94 | 72 |
| 54 | 93 | 0 |
| 56 | 95 | 33 |
| 57 | 100 | 61 |
| 58 | 100 | 65 |
| 62 | 100 | 77 |
| 64 | 100 | 96 |
| Comp. Compound (1) | 0 | 0 |
| Comp. Compound (2) | 0 | 0 |
| Comp. Compound (3) | 0 | 0 |
| Untreated | 0 | 0 |

Comparative Compound (1): 1-{(tetrahydro-2-furanyl)-methylamino}-1-methylamino-2-nitroethylene
Comparative Compound (2): 1-{(2-furylmethyl)amino}-1-methylamino-2-nitroethylene

Test Example 5

Effect on *Blattella germanica* Linne—German cockroach:

The compound of the invention was dissolved in acetone and diluted with acetone to a predetermined concentration. The acetone solution was applied on the bottom face of a Tall-skirted dish (height:9 cm, diameter:9 cm). After drying the dish in air, ten male adults of German cockroach were released therein. After hours, the mortality was checked. The results are shown in Table 9.

TABLE 9

Effect on *Blatella germanica* Linne - german cockroach

| Test Compound | Mortality (%) 1000 ppm | 100 ppm |
|---|---|---|
| Nos. 1 | 100 | 100 |
| 20 | 100 | 100 |
| 35 | 100 | 100 |
| 58 | 100 | 100 |
| Comp. Compound (4) | 0 | 0 |
| Untreated | 0 | 0 |

Comparative Compound (4): 3-{(2-chloropyridine-5-yl)-methyl}-1-methyl-2-nitroguanidine (compound described in Japanese Patent Laid-Open No. 157308/1991)

Next, explanation is made concretely by-way of the following test examples to clarify the insecticidal activity of the intermediates of the formula (2) according to the present invention.

Test Example 6

Effect on *Laodelphax striatellus* Fallen—smaller brown planthopper:

The compound of the invention was dissolved in acetone to a predetermined concentration and 3 ml of the acetone solution was applied over a bundle of several rice seedlings (about 3rd leaf stage). After drying in air, the treated seedlings were covered with a metal gauze cylinder, in which ten female adults of smaller brown planthopper were released, followed by placing in a temperature controlled room at 25° C. After 48 hours, the mortality was checked. The results are shown in Table 10.

TABLE 10

Effect on *Laodelphax striatellus* Fallen - smaller brown planthopper

| Test Compound | Mortality (%) 100 ppm |
|---|---|
| Nos. A1 | 30 |
| A2 | 100 |
| A5 | 100 |
| A6 | 100 |
| Comp. Compound (5) | 0 |
| Untreated | 0 |

Comparative Compound (5): 1-{(tetrahydro-2-furanyl)-methylamino}-2-nitroimino-5-methylhexahydro-1,3,5-triazine

Test Example 7 cEffect on resistant strain of *Nephotetrix cincticeptus* Uhler—resistant green rice leafhopper:

The compound of the invention was dissolved in acetone to a predetermined concentration and 3 ml of the acetone solution was applied on a bundle of several rice seedlings (about 3rd leaf stage). After drying in air, the treated seedlings were covered with a metal gauze cylinder, in which ten female adults of resistant green rice leafhopper were released, followed by placing in temperature controlled room at 25° C. After 48 hours, the mortality was checked. The results are shown in Table 11.

TABLE 11

Effect on resistant strain of *Nephotettix cincticeptus* Uhler - resistant green rice leafhopper

| Test Compound | Mortality (%) 100 ppm |
|---|---|
| Nos. A1 | 100 |
| A2 | 100 |
| A5 | 100 |
| A6 | 100 |
| A7 | 100 |
| Comp. Compound (5) | 0 |
| Untreated | 0 |

Comparative Compound (5): 1-{(tetrahydro-2-furanyl)-methylamino}-2-nitroimino-5-methylhexahydro-1,3,5-triazine

What is claimed is:

1. A compound of a formula (2):

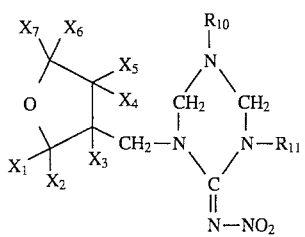

where $X_1$, $X_2$, $X_3$, $X_4$, $X_5$, $X_6$ and $X_7$ represent each a hydrogen atom or an alkyl group having from 1 to 4 carbon atoms; $R_{10}$ represents an alkyl group having from 1 to 5 carbon atoms or a benzyl group; and $R_{11}$ represents an alkyl group having from 1 to 5 carbon atoms or a benzyl group.

2. The compound of claim 1 wherein $X_1$, $X_2$, $X_3$, $X_4$, $X_5$, $X_6$ and $X_7$ are each a hydrogen atom.

3. The compound of claim 2 wherein $R_{10}$ and $R_{11}$ are each a methyl group.

* * * * *